US011083756B2

(12) United States Patent
Stewart et al.

(10) Patent No.: US 11,083,756 B2
(45) Date of Patent: Aug. 10, 2021

(54) SERUM-FREE AND XENOGEN-FREE HUMAN CARDIAC EXPLANT-DERIVED STEM CELLS AND USES AND METHODS FOR THE PRODUCTION THEREOF

(71) Applicant: Ottawa Heart Institute Research Corporation, Ottawa (CA)

(72) Inventors: Duncan J. Stewart, Ottawa (CA); David Courtman, Ottawa (CA); Seth Mount, Ottawa (CA); Darryl Davis, Ottawa (CA)

(73) Assignee: OTTAWA HEART INSTITUTE RESEARCH CORPORATION, Ottawa (CA)

( * ) Notice: Subject to any disclaimer, the term of this patent is extended or adjusted under 35 U.S.C. 154(b) by 0 days.

(21) Appl. No.: 15/608,691

(22) Filed: May 30, 2017

(65) Prior Publication Data
US 2017/0340678 A1    Nov. 30, 2017

Related U.S. Application Data

(60) Provisional application No. 62/343,052, filed on May 30, 2016.

(51) Int. Cl.
*A61K 35/34* (2015.01)
*C12N 5/077* (2010.01)
*A61K 9/00* (2006.01)

(52) U.S. Cl.
CPC ............ *A61K 35/34* (2013.01); *A61K 9/0019* (2013.01); *C12N 5/0657* (2013.01); *C12N 2500/02* (2013.01); *C12N 2500/38* (2013.01); *C12N 2500/44* (2013.01); *C12N 2500/62* (2013.01); *C12N 2500/90* (2013.01); *C12N 2500/98* (2013.01); *C12N 2501/119* (2013.01); *C12N 2501/155* (2013.01); *C12N 2533/52* (2013.01)

(58) Field of Classification Search
CPC .. A61K 35/34; C12N 5/0657; C12N 2500/02; C12N 2500/38; C12N 2500/44; C12N 2500/62; C12N 2500/90; C12N 2500/98; C12N 2501/119; C12N 2501/155; C12N 2533/52
See application file for complete search history.

(56) References Cited

U.S. PATENT DOCUMENTS

| 8,119,123 | B2 | 2/2012 | Anversa et al. |
| 8,343,479 | B2 | 1/2013 | Anversa et al. |
| 8,512,696 | B2 | 8/2013 | Anversa et al. |
| 8,623,351 | B2 | 1/2014 | Anversa et al. |
| 8,663,627 | B2 | 3/2014 | Anversa |
| 2007/0282456 | A1* | 12/2007 | Geng .................. C12N 5/0657 623/23.76 |
| 2012/0039857 | A1* | 2/2012 | Smith .................. C12N 5/0657 424/93.7 |
| 2013/0095080 | A1* | 4/2013 | Bernstein ............... A61K 35/28 424/93.7 |
| 2014/0271616 | A1* | 9/2014 | Nejadnik ............. C12N 5/0662 424/130.1 |

OTHER PUBLICATIONS

Patrikoski et al., Stem Cell Research & Therapy, 2013, 4:27, p. 1-15 (Year: 2013).*
Datasheet, Collagenase NB 6 GMP grade, http://www.serva.de (Year: 2018).*
Aldridge, Pharmaceutical Technology Europe, vol. 19, Issue 2, 2007 (Year: 2007).*
Beltrami et al. Adult Cardiac Stem Cells Atre Multipotent and Support Myocardial Regeneration, Cell vol. 114, 763-776 (Year: 2003).*
Usta et al., Annals of Translated Medicine 2014 2(10):97,1-9 (Year: 2014).*
Chase et al., Stem Cells Translational Medicine 2012;1:750-758 (Year: 2012).*
Passier et al., Stem Cells 2005;23:772-780 (Year: 2005).*
ThermoFisher Scientific, Gibco Growth Factors: https://www.thermofisher.com/us/en/home/life-science/cell-culture/mammalian-cell-culture/recombinant-proteins/growth-factors.html (Year: 2020).*
Gibco Life Technologies, CELLstart CTS (Year: 2014).*
McKay, "What does Xeno-Free really mean, and why does it matter to cell culture scientists today?", Mar. 2016, https://cellculturedish.com/what-does-xeno-free-really-mean-and-why-does-it-matter-to-cell-culture-scientists-today/ (Year: 2016).*
BI, Biological Industries Instructions Brochure, NutriStem® hPSC XF, 2008 (3 pages).
Ditte Caroline Andersen et al., Murine "Cardiospheres" Are Not a Source of Stem Cells with Cardiomyogenic Potential, Stem Cells, Tissue-Specific Stem Cells, 2009; 27, pp. 1571-1581. www.StemCells.com.
Isotta Chimenti et al., "Serum and Supplement Optimization for EU GMF-Compliance in Cardiospheres Cell Culture", J. Cell. Mol. Med., vol. 18, No. 4. 2014, pp. 624-634.
Darryl R. Davis et al., "Validation of the Cardiosphere Method to Culture Cardiac Progenitor Cells from Myocardial Tissue", Heart Institute, Cedars-Sinai Medical Center, PLoS One Sep. 1, 2009, vol. 4, Issue 9, e7195, 8 pages. www.plosone.org.
Lincoln T. Shenje et al., "Lineage Tracing of Cardiac Explant Derived Cells, PLoS One , Apr. 2008, vol. 3, Issue 4, e1929, 10" pages. www.plosone.org.

(Continued)

Primary Examiner — Ruth A Davis
(74) Attorney, Agent, or Firm — Winston & Strawn LLP

(57) ABSTRACT

Methods for generating serum-free and/or xenogen-free cardiac explant-derived stem cells (EDC) are provided. These methods may include providing an initial cardiac explant, which has been minced and digested; plating the initial cardiac explant; culturing the plated cardiac explant in serum-free and xenogen-free medium; harvesting EDC cells surrounding or emerging from the plated cardiac explant; and optionally performing static expansion of harvested EDC cells in serum-free and xenogen-free media. Serum-free and/or xenogen-free cardiac EDC cells produced by these methods, as well as methods and uses thereof for the treatment of heart failure in a subject in need thereof, are also provided.

21 Claims, 11 Drawing Sheets

(56) References Cited

OTHER PUBLICATIONS

Seth Mount et al., "Physiologic Expansion of Human Heart Derived Cells Enhances Therapeutic Repair of Injured Myocardium", Stem Cell Research & Therapy (2019) 10:316, 16 pages.

* cited by examiner

Serum EDCs

SF EDCs exSF EDCs

Serum EDCs

SF EDCs exSF EDCs

SERUM-FREE AND XENOGEN-FREE HUMAN CARDIAC EXPLANT-DERIVED STEM CELLS AND USES AND METHODS FOR THE PRODUCTION THEREOF

This application claims the benefit of application No. 62/343,052 filed May 30, 2016, the entire content of which is expressly incorporated herein by reference thereto.

FIELD OF INVENTION

The present invention relates generally to explant-derived stem cells (EDC). More specifically, the present invention relates to serum-free EDC cells, and uses and methods for the production thereof.

BACKGROUND

Mechanical and pharmaceutical advances in cardiac care have dramatically reduced the mortality associated with myocardial infarction. As a result, health care systems are faced with a growing number of patients living with chronic heart failure—a diagnosis that still carries a 5-year mortality rate approaching 50% [1, 2]. This observation reflects the ability of current therapies to slow the progression of heart failure without addressing the loss of functional myocardium.

Cell therapy using ex vivo proliferated cell products has since emerged as a promising means of replacing lost myocardium with potential for translation into the clinic. Amongst the cell candidates sourced from adult heart tissue, explant-derived cells have become the standard initial cells grown from plated heart tissue for further antigenic selection (i.e., c-Kit+ cells) or sphere culture (i.e., cardiosphere-derived cells (CDCs)) [3-6]. Phase I clinical trials using EDC-sourced c-Kit+ cells or CDCs have shown these cells to be safe with hints of efficacy that remain to be confirmed in Phase II trials (4-7). EDCs provide a complimentary admixture of progenitor cells that promote myocardial repair through indirect paracrine effects and differentiation into myocardium [7-11, 27, 28].

Translating cardiac-derived cell products to the clinic is expected to be problematic, as traditional culture media are typically supplemented with ill-defined or xenobiotic components such as fetal bovine serum. While recent studies have investigated the effects of replacing fetal bovine serum with commercially-available human-sourced alternatives [12], the inherent variability and potential for infectious or toxic contaminants make these approaches sub-optimal. Furthermore, altering EDC culture conditions is not straightforward, as several divergent culture methods have been shown to profoundly impair the regenerative performance of cardiac-derived cell products in certain examples [13-15].

An alternative, additional, and/or improved explant-derived stem cell and/or method for the product thereof is desirable.

SUMMARY OF INVENTION

Traditionally, culture conditions used to proliferate cells from plated cardiac tissue are supplemented by ill-defined or xenobiotic components such as fetal bovine serum. Traditional methods also rely upon antigenic selection or prolonged cell culture. Previously, altering explant-derived cardiac stem cell culture conditions has not been straightforward, and divergent culture methods have been shown to impair regenerative performance of cardiac-derived cell products. The teachings herein, however, provide methods for generating serum-free and/or xenogen-free cardiac explant-derived stem cells (EDC). Methods described herein may provide for, for example, culturing of explant-derived cardiac stem cells from plated myocardial tissue/cardiac explants using serum-free and xenogen-free methods. Such serum-free (SF) cells may be capable of promoting therapeutic repair of injured myocardium, for example. Expansion of serum-free and xenogen-free cardiac explant-derived cell products is also described herein.

In an embodiment, there is provided herein a method for transitioning cardiac explant-derived stem cells (EDC) to serum-free (SF) and/or xenogen-free culture conditions, said method comprising:
  providing an initial cardiac explant, which has optionally been obtained from atrial appendages or myocardial, atrial, or ventricular biopsy, and which has been minced and digested with collagenase;
  plating the initial cardiac explant on a cell culture plate;
  culturing the plated cardiac explant in serum-free and/or xenogen-free medium;
  harvesting EDC cells surrounding or emerging from the plated cardiac explant using trypsin; and
  optionally, performing static expansion of harvested EDC cells on cultureware in serum-free and xenogen-free media,
  thereby transitioning cardiac EDC cells to serum-free (SF) and xenogen-free culture conditions.

In another embodiment, there is provided herein a method for producing a serum-free (SF) and/or xenogen-free culture of cardiac explant-derived stem cells (EDC), said method comprising:
  providing an initial cardiac explant, which has optionally been obtained from atrial appendages or myocardial, atrial, or ventricular biopsy, and which has been minced and digested with collagenase;
  plating the initial cardiac explant on a cell culture plate;
  culturing the plated cardiac explant serum-free and/or xenogen-free medium;
  harvesting EDC cells surrounding or emerging from the plated cardiac explant using trypsin; and
  optionally, performing static expansion of harvested EDC cells on cultureware in serum-free and xenogen-free media,
  thereby producing the serum-free and xenogen-free culture of cardiac EDC cells.

In still another embodiment, there is provided herein a method for preparing cardiac explant-derived stem cells (EDC) for clinical use, said method comprising:
  providing an initial cardiac explant, which has optionally been obtained from atrial appendages or myocardial, atrial, or ventricular biopsy, and which has been minced and digested with collagenase;
  plating the initial cardiac explant on a cell culture plate;
  culturing the plated cardiac explant in serum-free and/or xenogen-free medium;
  harvesting EDC cells surrounding or emerging from the plated cardiac explant using trypsin; and
  optionally, performing static expansion of harvested EDC cells on cultureware in serum-free and xenogen-free media,
  thereby preparing EDC cells for clinical use.

In another embodiment of any of the method or methods above, the collagenase may be collagenase I/II.

In still another embodiment of any of the method or methods above, the cell culture plate may be a fibronectin-coated plate.

In yet another embodiment of any of the method or methods above, the culturing may be performed at physiological oxygen tension of about 5%, or at ambient oxygen tension of about 21%.

In another embodiment of any of the method or methods above, the culturing may include supplementing with serum for an initial period, followed by full replacement with serum-free and/or xenogen-free medium. In certain further embodiments, the supplementing may comprise supplementing with about 2% serum. In still further embodiments, the initial period may be about 48 hours, or more than about 48 hours.

In another embodiment of any of the method or methods above, the cultureware may be fibronectin coated cultureware.

In yet another embodiment of any of the method or methods above, the cardiac explant-derived stem cells (EDC) may be human cardiac explant-derived stem cells (EDC).

In another embodiment of any of the method or methods above, the collagenase, the cell culture plate, the serum-free and xenogen-free medium, the trypsin, the cultureware, or any combination thereof, may be Good Manufacturing Practice (GMP)-grade. In certain embodiments, all of the cell culture plate, the serum-free and xenogen-free medium, the trypsin, and the cultureware are GMP-grade.

In another embodiment of any of the method or methods above, the serum-free and xenogen-free media may be Nutristem XF, or an equivalent thereof.

In another embodiment of any of the method or methods above, the trypsin may be TrypLE Select, or an equivalent thereof.

In yet another embodiment of any of the method or methods above, the static expansion may be performed for about 7 days.

In yet another embodiment of any of the method or methods above, the method may further comprise:
performing one or a plurality of the harvesting and static expansion steps, followed by cryogenic storage of the thus obtained EDC cells; and
recovering and, optionally, pooling the cryogenically stored EDC cells.

In another embodiment of any of the method or methods above, the harvesting and static expansion steps may be performed up to 5 times. In another embodiment, the pooled EDC cells may be for administration to a subject in need thereof as a single intra-myocardial or intra-coronary injection, or as multiple intra-myocardial or intra-coronary injections.

In yet another embodiment, there is provided herein a serum-free and/or xenogen-free cardiac explant-derived cell (EDC), produced by any of the method or methods above. In still another embodiment, the serum-free and/or xenogen-free cardiac EDC may be human.

In still another embodiment, there is provided herein a use of the serum-free and/or xenogen-free cardiac explant-derived cell (EDC) described above for the treatment of heart failure in a subject in need thereof, for repairing and/or regenerating tissue in a subject in need thereof, or a combination thereof. In certain embodiments, the tissue may be cardiac tissue.

In yet another embodiment, there is provided herein a method for treating heart failure and/or for repairing and/or regenerating tissue in a subject in need thereof, said method comprising:

transplanting serum-free and/or xenogen-free human cardiac explant-derived cells (EDC) as defined above into the subject; and
allowing the EDC to repair or replace injured or lost tissue, such as myocardium, in the subject.

In another embodiment, the serum-free and/or xenogen-free cardiac EDC cells may be administered to a subject in need thereof by intra-myocardial or intra-coronary injection.

In still another embodiment, the serum-free and/or xenogen-free human cardiac explant-derived cells (EDC) may be autologous for the subject.

In yet another embodiment, there is provided herein a kit comprising a serum-free and/or xenogen-free human cardiac explant-derived cell (EDC) as described above, and at least one of a serum-free and/or xenogen-free medium, a tool for injection of the EDC cells into the heart of a subject in need thereof, a collagenase, a cell culture plate, a trypsin, a cultureware, a vessel for the EDC cells, a differentiating signal or factor for causing the EDC cells to differentiate into cardiac tissue, instructions for culturing the EDC cells under serum-free and/or xenogen-free conditions, instructions for injecting the EDC cells into the heart of a subject in need thereof, a pharmaceutically acceptable carrier, diluent, buffer, excipient, or any combination thereof.

In yet another embodiment, there is provided herein a composition comprising a serum-free, xenogen-free cardiac explant-derived cell (EDC) as defined above, and at least one of a serum-free and/or xenogen-free medium, a pharmaceutically acceptable carrier, a pharmaceutically acceptable diluent, a pharmaceutically acceptable buffer, or a pharmaceutically acceptable excipient. In another embodiment, the composition may comprise a differentiating signal or factor for causing the EDC cells to differentiate into cardiac tissue.

In yet another embodiment, there is provided herein a method, use, cell, kit, or composition as described anywhere herein.

In still another embodiment, there is provided herein a serum-free and/or xenogen-free cardiac explant-derived stem cell (EDC). In yet another embodiment, there is provided herein a serum-free and/or xenogen-free cardiac explant-derived stem cell (EDC) culture. In certain embodiments, the serum-free and/or xenogen-free cardiac explant-derived stem cell (EDC) may be an EDC which has not been expanded. In certain embodiments, the EDC may be an expanded EDC.

In yet another embodiment, serum-free and/or xenogen-free cardiac explant-derived stem cells (EDCs) as described herein may be genetically reprogrammed into pluripotent stem cells using defined factors.

DETAILED DESCRIPTION

Figure 1:
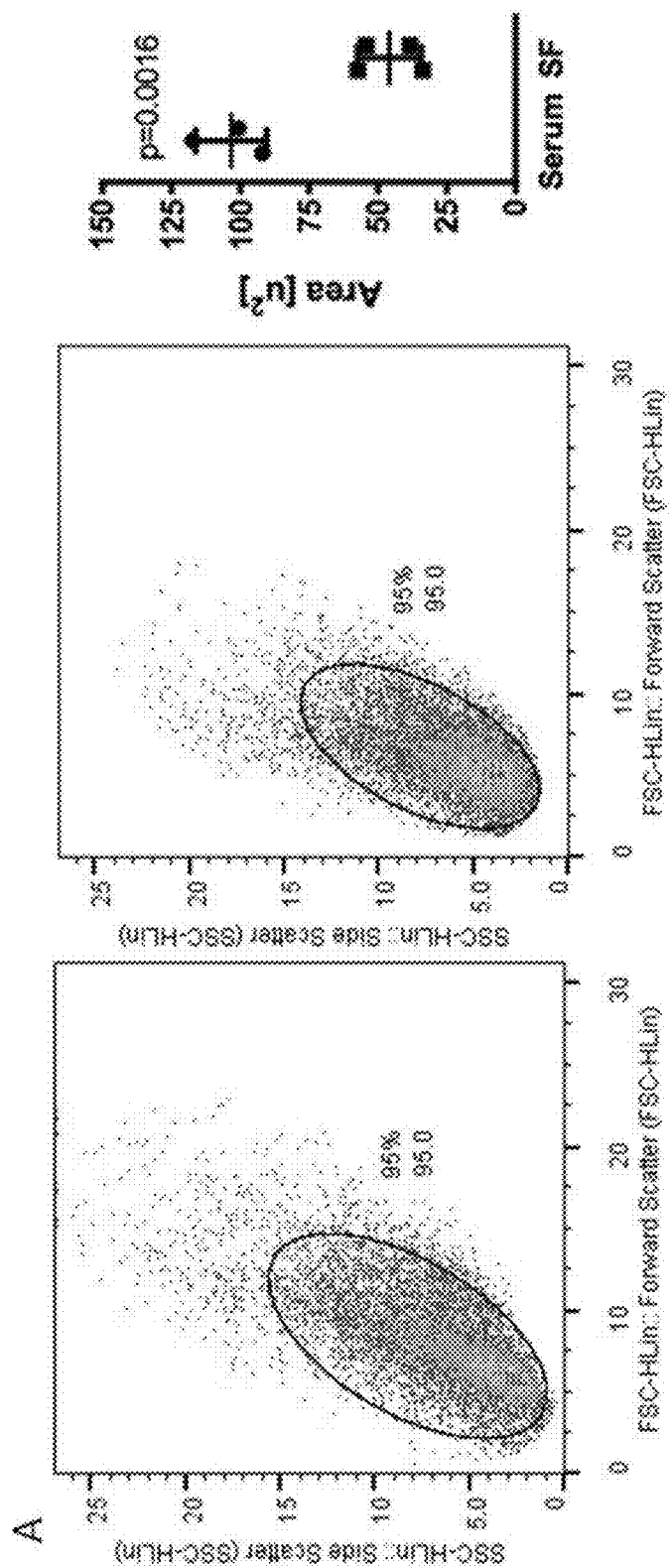
FIG. 1 shows effects of serum free GMP compatible culture conditions on EDC phenotype. (A) Flow cytometry demonstrating that the cells cultured in serum-free medium were smaller and more homogenous than cells cultured in standard 20% serum supplemented media conditions (mean±SEM, n=5 explant cultures). (B) Effect of transitioning explant digestion from standard (STD) laboratory grade to GMP compliant collagenase on c-Kit and CD90 content of serial weekly harvests from explant culture conditions (mean±SEM, n=5 explant cultures). (C) and (D) Effect of initial and expanded serum free culture conditions on the phenotypic make-up of EDCs (mean±SEM, *p<0.05 vs. standard 20% serum culture; n=5 explant cultures)
Figure 1:
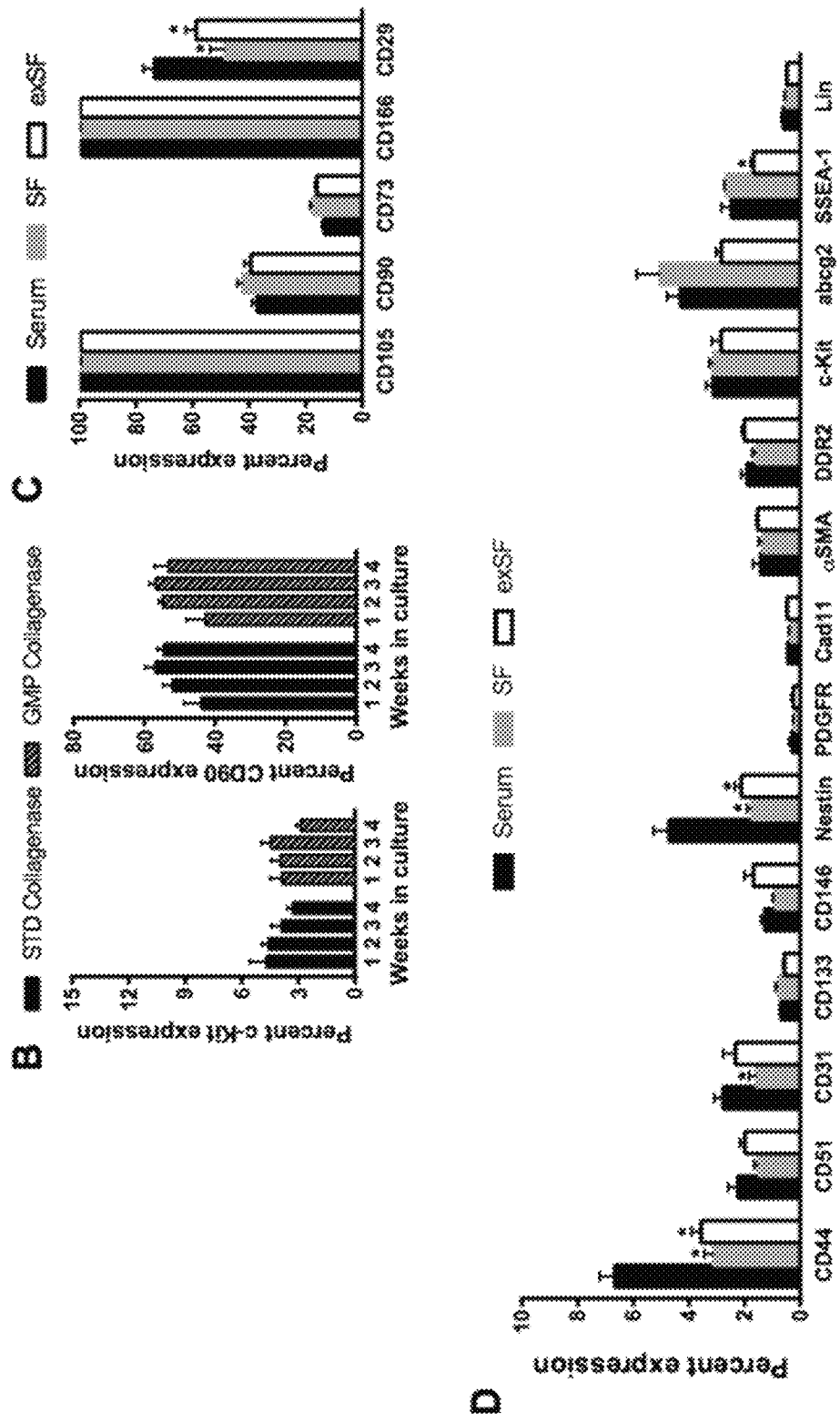

Straightforward clinical translation of autologous cardiac-derived stem cell therapies is limited by traditional culture conditions that are supplemented by ill-defined or xenobiotic components such as fetal bovine serum. Overcoming these barriers may be a critical step in developing next generation cardiac-derived cell therapies for clinical use.

Described herein are serum-free (SF) cardiac explant-derived stem cells (EDC), uses, and methods for the production thereof. It will be appreciated that embodiments and examples are provided herein for illustrative purposes intended for those skilled in the art, and are not meant to be limiting in any way.

Herein, the influence of a commercially sourced serum-free xenogen-free medium on human EDC yield, phenotype, in vitro measures of EDC performance, and post infarct cardiac repair is investigated. Given that EDCs are the initial cell product used for sphering or antigenic selection, EDCs provide a useful platform for testing the immediate effects of altered culture conditions, as it permits early detection of adverse changes that would directly influence the regenerative performance of downstream progeny. To reduce the possibility of contamination by materials used in tissue or cell processing, the need for each constituent of the EDC culture protocol was first established then replaced with a good manufacturing practices (GMP) compatible standard prior to testing in vitro and in vivo measures of EDC regenerative performance. The effect of straightforward expansion of this serum-free xenogen-free EDC product on cell-mediated repair of injured myocardium was then investigated as a means of simplifying expansion to clinically relevant "doses" while avoiding culture-acquired phenotypic drift and the risk of malignant transformation [16]. As well, the impact of altered culture practices on measures of EDC viability and stability were established to reduce logistical concerns surrounding transport and delivery to areas of injured myocardium.

As described in further detail below, cardiac explant-derived stem cell (EDC) cultures were transitioned to serum-free, xeno-free culture conditions (SF). These transitioned EDC cells demonstrated negligible effects on overall cell numbers, irrespective of explant tissue source. Flow cytometric morphometry demonstrated that SF conditions provided a smaller, more homogenous cell product with only minor effects on antigenic signature of EDCs. Despite reduced production of several pro-cardiogenic cytokines, SF EDCs promoted similar vessel formation, circulating stem cell recruitment and cardiogenic differentiation as compared to standard cultures. Under the conditions tested, static expansion of SF EDCs provided a 5-fold increase in cell numbers after 1 week of culture with negligible effects on cell content, paracrine production and in vitro measures of regenerative performance. Transplant of SF EDCs into immunodeficient mice 1 week after myocardial infarction boosted post ischemic repair by enhancing viable myocardium within the infarct. Expansion within SF media provided greater amounts of cells for delivery, but attenuated that ability of cells to promote post-infarct cardiac function. Storage of cell suspensions and injection through clinically approved intracoronary or trans-endocardial delivery systems did not alter cell viability, while facilitating successful product delivery to the peri-infarct zone. These results indicate that serum-free culture methods may provide a cardiac-derived cell product with the potential for translation to clinical use.

In certain embodiments, methods for generating serum-free and/or xenogen-free cardiac explant-derived stem cells (EDC) as described herein may allow for exposing cells to standardized levels of growth hormones and/or exposing cells to standardized conditions, thereby providing a more consistent and/or uniform cell product. In certain other embodiments, certain of the methods as described herein may allow for relatively rapid production of serum-free and/or xenogen-free cardiac explant-derived stem cells (EDC).

In an embodiment, there is provided herein a method for transitioning cardiac explant-derived stem cells (EDC) to serum-free (SF) and/or xenogen-free culture conditions, said method comprising:
  providing an initial cardiac explant, which has optionally been obtained from atrial appendages or myocardial, atrial, or ventricular biopsy, and which has been minced and digested with collagenase;
  plating the initial cardiac explant on a cell culture plate;
  culturing the plated cardiac explant in serum-free and xenogen-free medium;
  harvesting EDC cells surrounding or emerging from the plated cardiac explant using trypsin; and
  optionally, performing static expansion of harvested EDC cells on cultureware in serum-free and xenogen-free media,
thereby transitioning cardiac EDC cells to serum-free (SF) and xenogen-free culture conditions.

In another embodiment, there is provided herein a method for producing a serum-free (SF) and/or xenogen-free culture of cardiac explant-derived stem cells (EDC), said method comprising:
  providing an initial cardiac explant, which has optionally been obtained from atrial appendages or myocardial, atrial, or ventricular biopsy, and which has been minced and digested with collagenase;
  plating the initial cardiac explant on a cell culture plate;
  culturing the plated cardiac explant in serum-free and xenogen-free medium;
  harvesting EDC cells surrounding or emerging from the plated cardiac explant using trypsin; and
  optionally, performing static expansion of harvested EDC cells on cultureware in serum-free and xenogen-free media,
thereby producing the serum-free and xenogen-free culture of cardiac EDC cells.

In yet another embodiment, there is provided herein a method for preparing cardiac explant-derived stem cells (EDC) for clinical use, said method comprising:
  providing an initial cardiac explant, which has optionally been obtained from atrial appendages or myocardial, atrial, or ventricular biopsy, and which has been minced and digested with collagenase;
  plating the initial cardiac explant on a cell culture plate;
  culturing the plated cardiac explant in serum-free and/or xenogen-free medium;
  harvesting EDC cells surrounding or emerging from the plated cardiac explant using trypsin; and
  optionally, performing static expansion of harvested EDC cells on cultureware in serum-free and xenogen-free media,
thereby preparing EDC cells for clinical use.

In certain embodiments, the serum-free and/or xenogen-free cardiac explant-derived stem cells (EDCs) may be EDCs which have not been expanded. In certain embodiments, the serum-free and/or xenogeny-free cardiac explant-derived stem cells (EDCs) may be EDCs which have been expanded.

As described in further detail herein, experimental data indicates that non-expanded serum-free EDCs (which comprise cells collected from the initial using mild enzymatic digestion for substantially immediate use or storage using, for example, cryopreservation) may provide a greater degree of therapeutic regeneration in certain applications as compared to serum-cultured or expanded EDCs. Expanded EDCs (which comprise cells that have been placed in static culture for, for example, about 1-2 weeks prior to collection using mild enzymatic digestion prior to use), in contrast, may be somewhat less therapeutically potent on a per cell basis than non-expanded serum-free EDCs according to experimental data described herein, however expansion may provide greater cell doses which may be used.

In yet other embodiments, serum-free and/or xenogen-free cardiac explant-derived stem cells (EDCs) as described herein may be genetically reprogrammed into pluripotent stem cells using defined factors. As will be understood, methods described herein may thus optionally include an additional step of genetically reprogramming the EDC cells into pluripotent stem cells.

In certain embodiments of any of the above methods, the collagenase may be collagenase I/II blend. In certain other embodiments, the cell culture plate may be a fibronectin-coated plate. In still further embodiments, the cultureware may be fibronectin coated cultureware. In still other embodiments, the culturing may be performed at physiological oxygen tension of about 5%, or at ambient oxygen tension of about 21%. In a preferred embodiment, the culturing may be performed at physiological oxygen tension of about 5%.

In certain embodiments of any of the above methods, the culturing may include supplementing with serum for an initial period, followed by full replacement with serum-free and xenogen-free medium. In certain further embodiments, the supplementing may comprise supplementing with about 2% serum. In still further embodiments, the initial period may about 48 hours, or more than about 48 hours.

The person of skill in the art having regard to the teachings herein will recognize that the cardiac explant-derived stem cells (EDC) described herein may be animal cells, preferably human cells. The skilled person having regard to the teachings herein will be able to select a suitable cell type for a given application.

In certain embodiments of any of the above methods, the collagenase, the cell culture plate, the serum-free and xenogen-free medium, the trypsin, the cultureware, or any combination thereof, may be GMP-grade. The person of skill in the art will recognize that such GMP-grade materials may be used to suit particular applications where such grade may be desirable. In particular embodiments, all of these materials may be GMP-grade.

In still other embodiments of any of the above methods, the serum-free and xenogen-free media may be Nutristem XF, or an equivalent thereof. The skilled person will be aware of equivalents to Nutristem XF serum-free and xenogen-free media, and will be able to readily determine whether a given media equivalent will be suitable for a particular application based on the teachings provided herein.

In yet other embodiments of any of the above methods, the trypsin may be TrypLE Select, or an equivalent thereof. The skilled person will be aware of equivalents to TrypLE Select, and will be able to readily determine whether a given media equivalent will be suitable for a particular application based on the teachings provided herein.

In yet other embodiments of any of the above methods, the static expansion may be performed for up to about 2 weeks. For example, the static expansion may be performed for about 6-9 days, or about 7 days, in certain embodiments.

In still other embodiments of any of the above methods, the method may additionally comprise:
  performing one or a plurality of the harvesting and static expansion steps, followed by cryogenic storage of the thus obtained EDC cells; and
  recovering and, optionally, pooling the cryogenically stored EDC cells.

In another embodiment of the above method, the harvesting and static expansion steps may be performed two or more times. For example, harvesting and static expansion steps may be performed up to about 5 times.

In still another embodiment of the above method, the pooled EDC cells may be for administration to a subject in need thereof as a single intra-myocardial or intra-coronary injection, or as multiple intra-myocardial or intra-coronary injections.

In one exemplary and non-limiting embodiment, a method as described above may comprise the following steps:

[1] Digesting minced human ventricular or atrial biopsies or atrial appendages in a GMP-grade blend of collagenase I/II (not standard collagenase IV);

[2] Plating digested myocardial explants tissue on GMP-grade fibronectin-coated plates (not standard fibronectin coated plates);

[3] Culturing plated myocardium cells in GMP-grade serum-free and (optionally) xenogen-free medium (such as, for example, Nutristem XF, Biological Industries) at physiological (5%) oxygen tension (not standard CEM or 21% oxygen);

[4] Optionally, supplementing with 2% serum for an initial period of 48 hours or longer—at which time a full replacement of serum free media may be made;

[5] Collecting/harvesting cells that surround the plated biopsy using GMP compatible TrypLE Select or an equivalent thereof (not standard trypsin);

[6] Optionally, performing static expansion of harvested cells seeded at 5% or more (for example, about 10%) confluency on GMP compatible fibronectin coated cultureware for about 7 days (or more, or less) in serum free media (not sphering of cells within cardiosphere media or expansion of cardiospheres in CEM adherent based culture to form cardiosphere derived cells);

[7] Optionally, performing multiple harvests of explant derived cells from the same plated cardiac tissue (up to 5 times), followed by static expansion and cryogenic storage of cells; and

[8] Optionally, recovering and pooling together cryogenic cells from the multiple harvests, for administration to patients as a single intra-myocardial or intra-coronary injection or as multiple intro-myocardial or intra-coronary injections.

The person of skill in the art will recognize that certain of the above steps may be substitutable or optional, depending on the particular application.

The skilled person will additionally recognize that in certain embodiments, atrial appendages may be surgically removed at the time of open heart surgery, for example, and ventricular or atrial biopsies may be obtained by guiding a catheter into the heart and taking small bites from the heart tissue, for example. The skilled person will be aware of suitable techniques for obtaining a suitable biopsy or appendage.

In another embodiment, there is provided herein a serum-free and/or xenogen-free cardiac explant-derived cell (EDC), produced by any of the methods described above. Without wishing to be bound by theory, such a cell may likely be considered a multipotent cell, or a stem cell which has been at least partially differentiated to cardiac tissue.

The person of skill in the art will further recognize that EDC cells may represent a collection of different cell populations which express markers of endothelial, mesenchymal, and stem cell identity.

As described herein, it has now been found that serum-free, xenogen-free cardiac explant-derived cells (EDC) and methods as described herein may exhibit, under the conditions tested, one or more of the following properties as compared to standard cultured EDCs (i.e., standard fibronectin, collagenase, and CEM):

a. EDC cells cultured in serum free (SF) medium may be smaller and more homogeneous than those cultured in standard serum-dependent media;

b. Transitioning tissue explant culture from commercial grade collagenase IV to GMP compliant collagenase I/II may not significantly influence overall cell culture yields;

c. Transitioning tissue explant culture from commercial grade collagenase IV to GMP compliant collagenase I/II may not significantly influence the major sub-population content (c-Kit+ or CD90+ cells) at each serial harvest from the plated tissue;

d. Culture of atrial appendage biopsies within SF conditions may not alter the overall cell culture yields as compared to standard serum culture;

e. Using a custom panel of 19 different surface antigens designed to reflect markers of cardiac, endothelial, mesenchymal and stem cell identity, SF GMP conditions may reduce the content of CD29, CD44, CD31 and Nestin cells within EDC cells;

f. Plating of EDC cells within SF media for adherent culture may provide about a 5.5±1.1-fold increase in cell numbers over 7 days with a population doubling time of about 73±11 hours;

g. With the exception of a minor decline in the proportion of SSEA-1+ cells (Δ1.0±0.1% p=0.01 vs SF culture), static expansion within SF media may have negligible effects on the antigenic profile of EDC cells using a custom panel of 19 surface molecules;

h. Tissue source may not alter the proliferative capacity of EDC cells from plated tissue as culture yields from ventricular biopsies were maintained in the SF medium;

i. Multiplex profiling of the cytokine content within EDC conditioned media demonstrated SF culture and expansion within SF conditions had equivalent effects on cytokines known to promote cardiac repair SDF-1α, SCF, HGF, and VEGF-A, while SF conditions reduced the production of the pro-inflammatory cytokine IL-6;

j. Using xenogenic transplant of human EDC cells into immunodeficient mice, animals treated with intramyocardial injection of SF EDC cells showed, under the conditions tested, superior improvements in echocardiographic ejection fraction 3 weeks after cell treatment compared to animals that receiving traditional serum cultured EDC cells; and/or k. The regenerative advantages conferred by administering cells cultured in SF conditions was reduced in animals that received equivalent "cell doses" of expanded SF EDC cells to an extent that was comparable to animals who received cells cultured in standard serum conditions.

Methods as described herein may thus provide a serum-free and xenogen-free cell product that may have certain advantages to standard cultured EDC cells under the conditions tested. SF EDC cells may, for example, be expandable to relevant cell doses (i.e. 100 million cells) that may be available for cell injection within about 6 weeks of biopsy (vs. 8-10 weeks in the case of CDCs and 12+ weeks for c-Kit+ cells).

Figure 5:
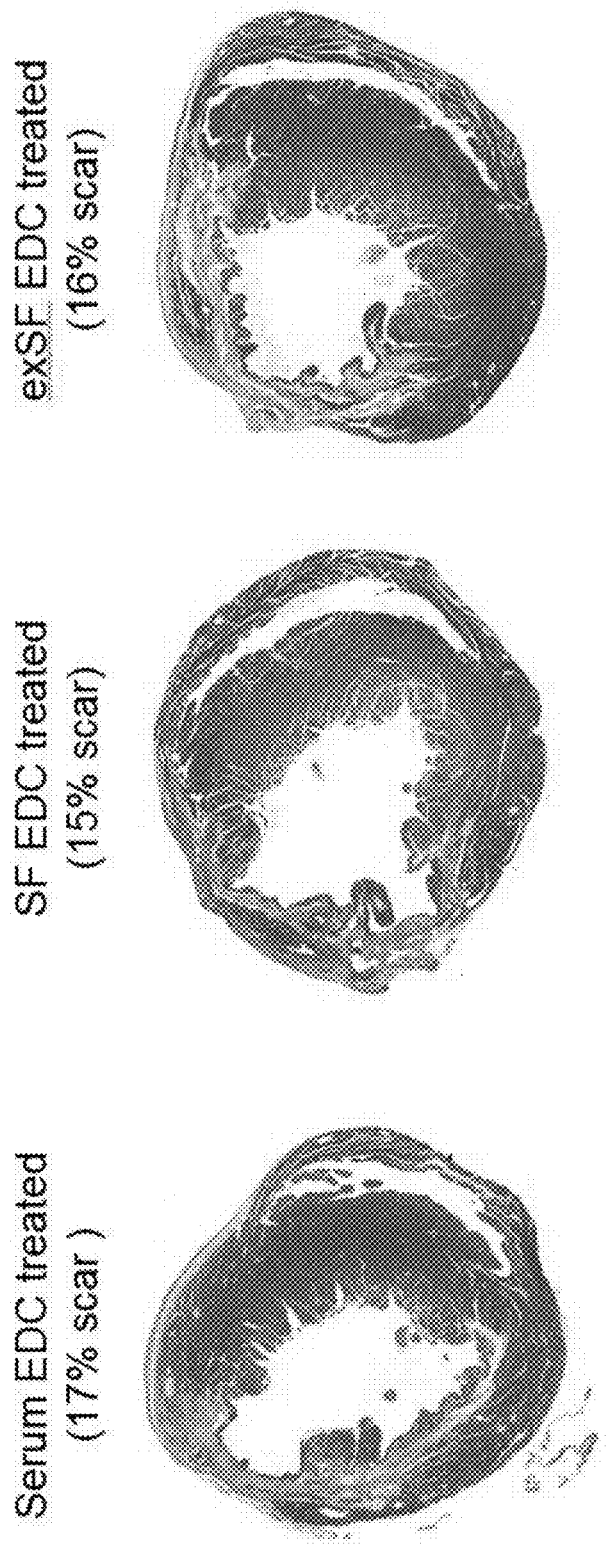
FIG. 5 shows representative short axis sections from animals randomized to transplant of serum, serum-free (SF) or expanded serum free (exSF) cultured EDCs. These typical sections were stained with Massons trichrome prior to imaging and scar (blue) was manually traced and quantified using Image J. Also shown is the measure of scar size obtained for each image.

EDC cells, as opposed to CDCs, may possess, for example, about a 1000-fold greater ability to adopt a cardiogenic phenotype (see FIG. 5 in Davis, Kizana et al. 2010). This may translate into greater direct replacement of myocardium if significant engraftment of transplanted cells can be realized. Standard cultured EDCs have been shown to provide comparable myocardial repair when compared to CDCs (Davis, Kizana et al., 2010). CDCs have been shown to provide superior cardiac repair when compared to antigenically selected c-Kit+ cells (Cheng, Shen et al., 2012).

Findings as described herein are somewhat surprising, as altered culture conditions have clearly been previously shown to have negative effects on EDC cell culture outcomes (Shenje, Field et al. 2008, Andersen, Andersen et al., 2009, Davis, Zhang et al. 2009).

In yet another embodiment, there is provided herein a use of a serum-free, xenogen-free cardiac explant-derived cell (EDC) as described herein for the treatment of heart failure in a subject in need thereof.

In still another embodiment, there is provided herein a method for treating heart failure in a subject in need thereof, said method comprising:

transplanting serum-free, xenogen-free cardiac explant-derived cells (EDC) as defined herein into the subject; and allowing the EDC to repair or replace injured or lost myocardium in the subject.

In certain embodiments, such uses and methods as described above may involve administration to the subject by intra-myocardial or intra-coronary injection. Such techniques are described in, for example, the references provided in Table 1 below, which are briefly outlined in Tables 2-4.

TABLE 1

References Pertaining to Intra-Myocardial and Intra-Coronary Injection

| Reference Number (as referenced in Table 2-4 below) | Citation |
|---|---|
| 1 | Makkar RR, Smith RR, Cheng K, Malliaras K, Thomson LE, Berman D, Czer LS, Marban L, Mendizabal A, Johnston PV, Russell SD, Schuleri KH, Lardo AC, Gerstenblith G and Marban E. Intracoronary cardiosphere-derived cells for heart regeneration after myocardial infarction (CADUCEUS): a prospective, randomised phase 1 trial. *Lancet*. 2012; 379: 895-904. |
| 2 | Malliaras K, Makkar RR, Smith RR, Cheng K, Wu E, Bonow RO, Marban L, Mendizabal A, Cingolani E, Johnston PV, Gerstenblith G, Schuleri KH, Lardo AC and Marban E. Intracoronary cardiosphere-derived cells after myocardial infarction: evidence of therapeutic regeneration in the final 1-year results of the CADUCEUS trial (CArdiosphere-Derived aUtologous stem CElls to reverse ventricUlar dySfunction). *J Am Coll Cardiol*. 2014; 63: 110-122. |
| 3 | Chugh AR, Beache GM, Loughran JH, Mewton N, Elmore JB, Kajstura J, Pappas P, Tatooles A, Stoddard MF, Lima JA, Slaughter MS, Anversa P and Bolli R. Administration of cardiac stem cells in patients with ischemic cardiomyopathy: the SCIPIO trial: surgical aspects and interim analysis of myocardial function and viability by magnetic resonance. *Circulation*. 2012; 126: S54-S64. |

TABLE 1-continued

References Pertaining to Intra-Myocardial and Intra-Coronary Injection

| Reference Number (as referenced in Table 2-4 below) | Citation |
|---|---|
| 4 | Bolli R, Chugh AR, D'Amario D, Loughran JH, Stoddard MF, Ikram S, Beache GM, Wagner SG, Leri A, Hosoda T, SanadaF, Elmore JB, Goichberg P, Cappetta D, Solankhi NK, Fahsah I, Rokosh DG, Slaughter MS, Kajstura J and Anversa P. Cardiac stem cells in patients with ischaemic cardiomyopathy (SCIPIO): initial results of a randomised phase 1 trial. *Lancet.* 2011; 378: 1847-1857, |
| 5 | Autologous Human CArdiac Derived Stem Cells to Treat Ischemic cArdiomyopathy (ALCADIA). 2009. |
| 6 | Bolli R, Tang XL, Sanganalmath SK, Rimoldi O, Mosna F, Abdel-Latif A, Jneid H, Rota M, Leri A and Kajstura J. Intracoronary delivery of autologous cardiac stem cells improves cardiac function in a porcine model of chronic ischemic cardiomyopathy. *Circulation.* 2013; 128: 122-131. |
| 7 | Crisostomo V, Baez-Diaz C, Maestre J, Garcia-Lindo M, Sun F, Casado JG, Blazquez R, Abad JL, Palacios I, Rodriguez-Borlado L and Sanchez-Margallo FM. Delayed administration of allogeneic cardiac stem cell therapy for acute myocardial infarction could ameliorate adverse remodeling: experimental study in swine. *J Transl Med.* 2015; 13: 156. |
| 8 | Gallet R, Tseliou E, Dawkins J, Middleton R, Valle J, Angert D, Reich H, Luthringer D, Kreke M, Smith R, Marban L and Marban E. Intracoronary delivery of self-assembling heart-derived microtissues (cardiospheres) for prevention of adverse remodeling in a pig model of convalescent myocardial infarction. *Circ Cardiovasc Interv.* 2015; 8. |
| 9 | Johnston PV, Sasano T, Mills K, Evers R, Lee ST, Smith RR, Lardo AC, Lai S, Steenbergen C, Gerstenblith G, Lange R and Marban E. Engraftment, differentiation, and functional benefits of autologous cardiosphere-derived cells in porcine ischemic cardiomyopathy. *Circulation.* 2009; 120: 1075-1083. |
| 10 | Lee ST, White AJ, Matsushita 5, Malliaras K, Steenbergen C, Zhang Y, Li TS, Terrovitis J, Yee K, Simsir S, Makkar R and Marban E. Intramyocardial injection of autologous cardiospheres or cardiosphere-derived cells preserves function and minimizes adverse ventricular remodeling in pigs with heart failure post-myocardial infarction. *J Am Coll Cardiol.* 2011; 57: 455-465. |
| 11 | Malliaras K, Smith RR, Kanazawa H, Yee K, Seinfeld J, Tseliou E, Dawkins JF, Kreke M, Cheng K, Luthringer D, Ho CS, Blusztajn A, Valle I, Chowdhury S, Makkar RR, Dharmakumar R, Li D, Marban L and Marban E. Validation of contrast-enhanced magnetic resonance imaging to monitor regenerative efficacy after cell therapy in a porcine model of convalescent myocardial infarction. *Circulation.* 2013; 128: 2764-75. |
| 12 | Welt FG, Gallegos R, Connell J, Kajstura J, D'Amario D, Kwong RY, Coelho-Filho O, Shah R, Mitchell R, Leri A, Foley L, Anversa P and Pfeffer MA. Effect of cardiac stem cells on left-ventricular remodeling in a canine model of chronic myocardial infarction. *Circ Heart Fail.* 2013; 6: 99-106. |
| 13 | Williams AR, Hatzistergos KE, Addicott B, McCall F, Carvalho D, Suncion V, Morales AR, Da SJ, Sussman MA, Heldman AW and Hare JM. Enhanced effect of combining human cardiac stem cells and bone marrow mesenchymal stem cells to reduce infarct size and to restore cardiac function after myocardial infarction. *Circulation.* 2013; 127: 213-223. |
| 14 | Yee K, Malliaras K, Kanazawa H, Tseliou E, Cheng K, Luthringer DJ, Ho CS, Takayama K, Minamino N, Dawkins JF, Chowdhury S, Duong DT, Seinfeld J, Middleton RC, Dharmakumar R, Li D, Marban L, Makkar RR and Marban E. Allogeneic cardiospheres delivered via percutaneous transendocardial injection increase viable myocardium, decrease scar size, and attenuate cardiac dilatation in porcine ischemic cardiomyopathy. *PLoS One.* 2014; 9: e113805. |
| 15 | Stamm C, Westphal B, Kleine HD, Petzsch M, Kittner C, Klinge H, Schumichen C, Nienaber CA, Freund M and Steinhoff G. Autologous bone-marrow stem-cell transplantation for myocardial regeneration. *Lancet.* 2003; 361: 45-46. |
| 16 | Ahmadi H, Baharvand H, Ashtiani SK, Soleimani M, Sadeghian H, Ardekani JM, Mehrjerdi NZ, Kouhkan A, Namiri M, Madani-Civi M, Fattahi F, Shahverdi A and Dizaji AV. Safety analysis and improved cardiac function following local autologous transplantation of CD133(+) enriched bone marrow cells after myocardial infarction. *Curr, Neurovasc Res.* 2007; 4: 153-160. |
| 17 | Patel AN, Geffner L, Vina RF, Saslavsky J, Urschel J, Kormos R and Benetti F. Surgical treatment for congestive heart failure with autologous adult stem cell transplantation: A prospective randomized study. *The Journal of Thoracic and Cardiovascular Surgery.* 2005; 130: 1631-1631. |
| 18 | Zhao Q, Sun Y, Xia L, Chen A and Wang Z. Randomized study of mononuclear bone marrow cell transplantation in patients with coronary surgery. *Ann Thorac Surg.* 2008; 86: 1833-1840. |
| 19 | Stamm C, Kleine HD, Choi YH; Dunkelmann S, Lauffs JA, Lorenzen B, David A, Liebold A, Nienaber C, Zurakowski D, Freund M and Steinhoff G. Intramyocardial delivery of CD133+ bone marrow cells and coronary artery |

TABLE 1-continued

References Pertaining to Intra-Myocardial and Intra-Coronary Injection

| Reference Number (as referenced in Table 2-4 below) | Citation |
|---|---|
| | bypass grafting for chronic ischemic heart disease: safety and efficacy studies. *J Thorac Cardiovasc Surg*. 2007; 133: 717-725. |
| 20 | Patila T, Lehtinen M, Vento A, Schildt J, Sinisalo J, Laine M, Hammainen P, Nihtinen A, Alitalo R, Nikkinen P, Ahonen A, Holmstrom M, Lauerma K, Poyhia R, Kupari M, Kankuri E and Harjula A. Autologous bone marrow mononuclear cell transplantation in ischemic heart failure: a prospective, controlled, randomized, double-blind study of cell transplantation combined with coronary bypass. *J Heart Lung Transplant*. 2014; 33: 567-74. |
| 21 | Williams AR; Trachtenberg B, Velazquez DL, McNiece I, Altman P. Rouy D, Mendizabal AM, Pattany PM, Lopera GA, Fishman J, Zambrano JP, Heldman AW and Hare JM. Intramyocardial stem cell injection in patients with ischemic cardiomyopathy: functional recovery and reverse remodeling. *Circ Res*, 2011; 108: 792-796. |
| 22 | Heldman AW, DiFede DL, Fishman JE, Zambrano JP, Trachtenberg BH, Karantalis V, Mushtaq M, Williams AR, Suncion VY, McNiece IK, Ghersin E, Soto V, Lopera G, Miki R, Willens H, Hendel R, Mitrani R, Pattany P, Feigenbaum G, Oskouei B, Byrnes J, Lowery MH, Sierra J, Pujol MV, Delgado C, Gonzalez PJ, Rodriguez JE, Bagno LL, Rouy D, Altman P, Foo CW, da Silva J, Anderson E, Schwarz R, Mendizabal A and Hare JM. Transendocardial mesenchymal stem cells and mononuclear bone marrow cells for ischemic cardiomyopathy: the TAC-HFT randomized trial. *JAMA*. 2014; 311: 62-73. |
| 23 | Dohmann HF, Perin EC, Takiya CM, Silva GV, Silva SA, Sousa AL, Mesquita CT, Rossi MI, Pascarelli BM, Assis IM, Dutra HS, Assad JA, Castello-Branco RV, Drummond C, Dohmann HJ, Willerson JT and Borojevic R. Transendocardial autologous bone marrow mononuclear cell injection in ischemic heart failure: postmortem anatomicopathologic and immunohistochemical findings. *Circulation*. 2005; 112: 521-526. |
| 24 | Perin EC, Silva GV, Henry TD, Cabreira-Hansen MG, Moore WH, Coulter SA, Herlihy JP, Fernandes MR, Cheong BY, Flamm SD, Traverse JH, Zheng Y, Smith D. Shaw S. Westbrook L, Olson R, Patel D, Gahremanpour A, Canales J, Vaughn WK and Willerson JT. A randomized study of transendocardial injection of autologous bone marrow mononuclear cells and cell function analysis in ischemic heart failure (FOCUS-HF). *Am Heart J*. 2011; 161: 1078-1087. |
| 25 | Pokushalov E, Romanov A, Chernyaysky A, Larionov P, Terekhov I, Artyomenko S, Poveshenko O, Kliver E, Shirokova N, Karaskov A and Dib N. Efficiency of intramyocardial injections of autologous bone marrow mononuclear cells in patients with ischemic heart failure: a randomized study. *J Cardiovasc Transl Res*. 2010; 3: 160-8. |
| 26 | Perin EC, Sanz-Ruiz R, Sanchez PL, Lasso J, Perez-Cano R, Alonso-Farto JC, Perez-David E, Fernandez-Santos ME, Serruys PW, Duckers HJ, Kastrup J, Chamuleau S, Zheng Y, Silva GV, Willerson JT and Fernandez-Aviles F. Adipose-derived regenerative cells in patients with ischemic cardiomyopathy: The PRECISE Trial. *Am Heart J*. 2014; 168: 88-95 e2. |
| 27 | Mozid A, Yeo C, Arnous S, Ako E, Saunders N, Locca D, Brookman P, Archbold RA, Rothman M, Mills P. Agrawal S. Martin J and Mathur A. Safety and feasibility of intramyocardial versus intracoronary delivery of autologous cell therapy in advanced heart failure: the REGENERATE-IHD pilot study. *Regen Med*. 2014; 9: 269-78. |
| 28 | Hendrikx M, Hensen K, Clijsters C, Jongen H, Koninckx R, Bijnens E, Ingels M, Jacobs A, Geukens R, Dendale P, Vijgen J, Dilling D, Steels P, Mees U and Rummens JL. Recovery of regional but not global contractile function by the direct intramyocardial autologous bone marrow transplantation: results from a randomized controlled clinical trial. *Circulation*. 2006; 114: 1101-1107. |
| 29 | Perin EC, Willerson JT, Pepine CJ, Henry TD, Ellis SG, Zhao DX, Silva GV, Lai D, Thomas JD, Kronenberg MW, Martin AD, Anderson RD, Traverse JH, Penn MS, Anwaruddin S, Hatzopoulos AK, Gee AP, Taylor DA, Cogle CR, Smith D, Westbrook L, Chen J, Handberg E, Olson RE, Geither C, Bowman S, Francescon J, Baraniuk S, Piller LB, Simpson LM, Loghin C, Aguilar D, Richman S, Zierold C, Bettencourt J, Sayre SL, Vojvodic RW, Skarlatos SI, Gordon DJ, Ebert RF, Kwak M, Moye LA and Simari RD. Effect of transendocardial delivery of autologous bone marrow mononuclear cells on functional capacity, left ventricular function, and perfusion in chronic heart failure: the FOCUS-CCTRN trial. *JAMA*. 2012; 307: 1717-1726. |
| 30 | Duckers HJ, Houtgraaf J, Hehrlein C, Schofer J, Waltenberger J, Gershlick A, Bartunek J, Nienaber C, Macaya C, Peters N, Smits P, Siminiak T, van MW, Legrand V and Serruys PW. Final results of a phase IIa, randomised, open-label trial to evaluate the percutaneous intramyocardial transplantation of autologous skeletal myoblasts in congestive heart failure patients: the SEISMIC trial. *Eurointervention*. 2011; 6: 805-812. |

TABLE 1-continued

References Pertaining to Intra-Myocardial and Intra-Coronary Injection

| Reference Number (as referenced in Table 2-4 below) | Citation |
|---|---|
| 31 | Maureira P, Tran N, Djaballah W, Angioi M, Bensoussan D, Didot N, Fay R, Sadoul N, Villemot JP and Marie PY. Residual viability is a predictor of the perfusion enhancement obtained with the cell therapy of chronic myocardial infarction: a pilot multimodal imaging study. *Clin Nucl Med*. 2012; 37: 738-42. |
| 32 | Patel AN, Henry TD, Quyyumi AA, Schaer GL, Anderson RD, Toma C, East C, Remmers AE, Goodrich J, Desai AS, Recker D, DeMaria A and ix C-DCMI. Ixmyelocel-T for patients with ischaemic heart failure: a prospective randomised double-blind trial. *Lancet*. 2016. |
| 33 | Dib N, Dinsmore J, Lababidi Z, White B, Moravec S, Campbell A, Rosenbaum A, Seyedmadani K, Jaber WA, Rizenhour CS and Diethrich E. One-year follow-up of feasibility and safety of the first U.S., randomized, controlled study using 3-dimensional guided catheter-based delivery of autologous skeletal myoblasts for ischemic cardiomyopathy (CAuSMIC study). *JACC Cardiovasc Interv*, 2009; 2: 9-16. |
| 34 | Bartunek J, Behfar A, Dolatabadi D, Vanderheyden M, Ostojic M, Dens J, El Nakadi B, Banovic M, Beleslin B, Vrolix M, Legrand V, Vrints C, Vanoverschelde JL, Crespo-Diaz R, Homsy C, Tendera M, Waldman S, Wijns W and Terzic A. Cardiopoietic stem cell therapy in heart failure: the C-CURE (Cardiopoietic stem Cell therapy in heart failURE) multicenter randomized trial with lineage-specified biologics. *J Am Coll Cardiol*. 2013; 61: 2329-38. |

TABLE 2

Completed Randomized Clinical Trials Employing First Generation Human CSC Products for the Treatment of Heart Failure or Recent MI - Reference Numbers Refer to Table 1

|  | CADUCEUS[1, 2] | SCIPIO[3, 4] | ALCADIA[5] |
|---|---|---|---|
| Cell type | CDCs | c-Kit+ cells only | CDCs + bFGF hydro-gel |
| Number injected | 15-25 million | 500,000-1 million | 0.5 million per kg body weight |
| Route of administration | Intra-coronary injection |  | Surgical + intra-coronary injection |
| Population | Post ST elevation MI | Post CABG | Heart failure patients with chronic ischemic cardiomyopathy |
| Tissue Source | Cardiac Biopsy | Atrial Appendage | Atrial Appendage |
| Time from enrolment to injection | 65 ± 14 days | 113 ± 4 days | Study in progress |
| Safety | No increased adverse events | No increased adverse events | No increased adverse events |
| Benefit | Evidence for regeneration with trends for improved LVEF | Improved LVEF and reduced infarct size | Study in progress |

TABLE 3

Completed Pre-Clinical Trials Delivering Cardiac Stem Cells after MI.

|  | Species | Route | Treatment/ controls | Cell type + amount | Admin. Timing (after MI) | Assessment Timing (after therapy) | EF difference (95% confidence intervals) |
|---|---|---|---|---|---|---|---|
| Bolli et al.[6] | pig | IC | 11/10 | $5 \times 10^6$ c-Kit+ cells | 5 h | 20 d | 8.8 (2.9 to 14.7) |

TABLE 3-continued

Completed Pre-Clinical Trials Delivering Cardiac Stem Cells after MI.

| | Species | Route | Treatment/ controls | Cell type + amount | Admin. Timing (after MI) | Assessment Timing (after therapy) | EF difference (95% confidence intervals) |
|---|---|---|---|---|---|---|---|
| Crisostomo et al.[7] | pig | IC | 5 + 6/7 | $25 \times 10^6$ c-Kit+ cells | 2 h or 7 d | 10 wk | 4.2 (−6.7 to 15.1) 0.9 (−12.8 to 14.6) |
| Gallet et al.[8] | pig | IC | 7/7 | $1.3 \times 10^6$ Cps | 3 wk | 4 wk | 2.7 (0.4 to 5.0) |
| Johnston et al.[9] | pig | IC | 7/6 | $10^7$ CDCs | 4 wk | 8 wk | 0.6 (−10.5 to 11.7) |
| Lee et al.[10] | pig | EI | 10 + 8/11 | $2 \times 10^6$ Cps $2 \times 10^6$ CDCs | 4 wk | 4 wk | 7.0 (1.0 to 13.0) 4.0 (−2.4 to 10.4) |
| Malliaras et al.[11] | pig | IC | 5/5 | $12.5 \times 10^6$ CDCs | 2-3 wk | 8 wk | 9.3 (6.4 to 12.2) |
| Welt et al.[12] | dog | EI | 13/6 | $16 \times 10^6$ c-Kit+ cells | 6 wk | 24 wk | 6.5 (−0.4 to 13.4) |
| Williams et al.[13] | pig | EI | 5/5 | $1.6 \times 106$ c-Kit+ cells | 2 wk | 4 wk | 9.3 (0.9 to 17.7) |
| Yee et al.[14] | pig | TE | 4 + 4 + 4 + 6 | $15 \times 10^6$ Cps $45 \times 10^6$ Cps $150 \times 10^6$ Cps $150 \times 10^6$ Cps | 4 wk 4 wk 4 wk 8 wk | 4 wk 4 wk 4 wk 8 wk | −1.2 (−11.7 to 9.3) 1.1 (−7.9 to 10.1) 5.7 (2.0 to 9.4) 2.3 (−3.4 to 8.0) |

IC—Intracoronary; EI—Epicardial Injection; TE—Transendocardial; Cps—Cardiospheres; CDCs—Cardiosphere-derived cells.
Reference Numbers Refer to Table 1

TABLE 4

Completed Clinical Trials Delivering Stem Cells Later After MI.

| | Trial type | Number of cells | Age of infarct | Treated/ control | randomized | Change in LVEF (%) (Controls) | Change in LVEF (%) (Treated) | Follow-up |
|---|---|---|---|---|---|---|---|---|
| Epicardial injection | | | | | | | | |
| Stamm et al.,[15] | CABG + BMC | $1.5 \times 10^6$ | <3 months | 6/0 | N | NA | 12.7 | 3-10 months |
| Ahmadi et al.,[16] | CABG + BMC | $1.8 \times 10^6$ | <3 months | 18/9 | N | 5.2 | 3.7 | 14 months |
| Patel et al.,[17] | CABG + BMC | $2.2 \times 10^7$ | NA | 10/10 | Y | 6.6 | 16.6 | 6 months |
| Zhao et al.,[18] | CABG + BMC | $6.6 \times 10^8$ | 18 months | 18/18 | Y | 3 | 13 | 6 months |
| Stamm et al.,[19] | CABG + BMC | $7.5 \times 10^6$ | 2 weeks to 3 years | 20/20 | Y | 3.7 | 9.7 | 6 months |
| Patila et al,[20] | CABG + BMC | $840 \times 10^6$ | NA | 20/19 | Y | 5.6 | 4.8 | 12 months |
| Transendocardial injection | | | | | | | | |
| Williams et al.,[21] | BMC or MSC | N/A | >3 months | 8/0 | N | NA | 3 | 12 months |
| Heldman et al.,[22] | BMC or MSC | N/A | 7.7-15.1 years | 38/21 | Y | No change | No change | 12 months |
| Dohman et al.,[23] | BMC | $30 \times 10^6$ | >3 months | 14/7 | N | −4.15 | 5.5 | 2 months |
| Perin et al.,[24] | BMC | $30 \times 10^6$ | >3 months | 20/10 | Y | 4.8/0.9 | 3.5/4.5** | 6 months |
| Pokushalov et al.,[25] | BMC | $41 \times 10^6$ | 9 years | 49/33 | Y | −1.3 | 4.5 | 12 months |
| Perin et al.,[26] | ASC | $42 \times 10^6$ | NA | 21/6 | Y | NA | NA | 6 months |
| Mozid et al.,[27] | BMC | $51 \times 10^6$ | 13 years | 30/30 | Y | NA | NA | 6 months |
| Hendrikx et al.,[28] | MSC | $60 \times 10^6$ | 217 days | 11/12 | Y | 3.6 | 5.6 | 4 months |

TABLE 4-continued

Completed Clinical Trials Delivering Stem Cells Later After MI.

| | Trial type | Number of cells | Age of infarct | Treated/ control | randomized | Change in LVEF (%) (Controls) | Change in LVEF (%) (Treated) | Follow-up |
|---|---|---|---|---|---|---|---|---|
| Perin et al.,[29] | BMC | 100 × 10[6] | NA | 61/31 | Y | −1.3 | 1.3 | 6 months |
| Duckers et al.,[30] | SM | 150-800 × 10[6] | NA | 31/16 | Y | −0.1 | −1.4 | 6 months |
| Maureira et al.,[31] | BMC | 342 × 10[6] | 7 months | 7/7 | N | −4 | 0 | 6 months |
| Patel et al.,[32] | BMC | 40-200 × 10[6] | NA | 58/51 | Y | No change | No change | 12 months |
| Dib et al.,[33] | SM | 30-600 × 10[6] | 11-13 years | 12/11 | Y | NA | NA | 12 months |
| Bartunek et al.,[34] | MSC | 605-1,1681 0[6] | 2 months | 32/15 | Y | 0.2 | 7.0 | 24 months |

ASC—Adipose Stem Cell; LVEF—Left Ventricular Ejection Fraction; CABG—Coronary Artery Bypass Graft Surgery; BMC—Bone Marrow-Derived Cells; CPC—Circulating Progenitor Cells; MSC—Mesenchymal Stem Cells; SM—Skeletal Myoblasts;
*BMC/CPC/Control,
***Not Statistically Significant when Compared to Control Group.
Reference Numbers Refer to Table 1

The person of skill in the art having regard to the teachings herein will recognize that, in certain embodiments, the xenogen-free cardiac explant-derived cells (EDC) for treating heart failure and/or repairing or replacing injured, damaged, or lost myocardium in a subject may be cells which are autologous for the subject. In other words, the xenogen-free cardiac explant-derived cells (EDC) may be derived from the subject to be treated. While allogenic approaches are also contemplated herein, autologous approaches may provide certain advantages in terms of decreased risk of rejection, sensitization to foreign antigens, and/or disease transmission.

In yet another embodiment, there is provided herein a kit comprising a serum-free, xenogen-free cardiac explant-derived cell (EDC) as described herein, and at least one of a serum-free and xenogen-free medium, a tool for injection of the EDC cells into the heart of a subject in need thereof, a collagenase, a cell culture plate, a trypsin, a cultureware, a vessel for the EDC cells, a differentiating signal or factor for causing the EDC cells to differentiate into cardiac tissue, instructions for culturing the EDC cells under serum-free and xenogen-free conditions, instructions for injecting the EDC cells into the heart of a subject in need thereof, or any combination thereof.

In still another embodiment, there is provided herein a composition comprising a serum-free, xenogen-free cardiac explant-derived cell (EDC) as described herein, and a serum-free and xenogen-free medium. In still another embodiment, the composition may comprise a differentiating signal or factor for causing the EDC cells to differentiate into cardiac tissue.

The person of skill in the art having regard to the teachings herein will understand that a differentiating signal or factor for causing the EDC cells to differentiate into cardiac tissue may include, for example, miRNAs, siRNAs, or other small molecules. It is contemplated that such factors may be used to, for example, increase the cardiogenic potential of EDC cells as described herein and/or to partially differentiate EDC cells as described herein. In certain embodiments, it is contemplated that such differentiating signals or factors may be provided when the cells are expanding under static conditions. In certain embodiments, it is contemplated that the period of exposure may be, for example, about 1 day prior to transplantation, or about 1 week prior to transplantation.

The person of skill in the art having regard to the teachings herein will further recognize that it is contemplated that serum-free, xenogen-free cardiac explant-derived cells (EDC) as described here may be further prepared for clinical application in the treatment of, for example, heart failure, by performing genetic reprogramming/genetic modification to boost cytokine production, thus boosting EDC stem cell function as described in, for example, Tilokee et al., *Stem cells,* 2016, doi: 10.1002/stem.2373; and Jackson et al., *Journal of the American Heart Association,* 2015, 4:e002104. By way of example, in certain embodiments it is contemplated that EDC cells as described herein may be subjected to genetic reprogramming of the CD90+ subfraction within EDCs to over-express stromal cell derived factor 1 alpha or insulin-like growth factor 1, which may promote post infarct repair. Such approaches may involve lentivirus reprogramming, or other methods such as mini circle DNA, for example.

The person of skill in the art having regard to the teachings herein will further recognize that it is contemplated herein that serum-free, xenogen-free cardiac explant-derived cells (EDC) as described here may further be used in the treatment of, for example, heart failure, as part of methods involving cell encapsulation as described in, for example, Mayfield et al., *Biomaterials,* 2014, 35:133-142; or in WO 2004/058305.

The following examples are provided for illustrative purposes and are intended for the person of skill in the art. These examples are provided to demonstrate certain embodiments as described herein, and should not be seen as limiting in any way.

EXAMPLES

Materials and Methods

EDC Cell Isolation and Culture

EDC cultures were established from atrial appendages or ventricular biopsies obtained from patients undergoing clinically-indicated procedures. All protocols were approved by the University of Ottawa Heart Institute Research Ethics Board. Inclusion criteria for tissue donors consisted of patients between the ages of 18 and 80 who required cardiac surgery for coronary artery bypass grafting and/or valve surgery. Exclusion criteria included chronic infectious diseases (such as HIV, hepatitis), pregnant women or active sepsis. Each tissue sample was minced, washed and digested with standard collagenase IV (Life Technologies) or a GMP-grade blend of collagenase I/II (Roche) [17] before plating on GMP-grade fibronectin-coated plates in standard cardiac explant media (Iscove's Modified Dulbecco's Medium, 20% fetal bovine serum, 100 U/ml penicillin G, 100 ug/ml streptomycin, 2 mmol/l L-glutamine and 0.1 mmol/l 2-mercaptoethanol; all sourced from Life Technologies) or GMP-grade serum free xeno free medium (SF; Nutristem XF, Biological Industries) at physiological (5%) oxygen tension [7-11, 18, 19, 27, 28]. EDCs that spontaneously emerged from the plated tissue were harvested up to 4 times every 7 days using TrypLE Select (Life Technologies) with enumeration using a Neubauer hemocytometer. The effects of static expansion on cell numbers and phenotype were investigated using aliquots of harvested cells seeded at 10% confluency on fibronectin coated cultureware for 7 days. Given EDC culture generally provides a constant output return proportional to the amount of tissue plated and the desire for larger cell numbers, right atrial appendage specimens were used for these experiments, although it will be understood that these embodiments are non-limiting. Ventricular tissue was used in cell proliferation experiments, to evaluate the ability of GMP SF culture conditions to support proliferation from a tissue source readily harvested for potential clinical application.

Circulating angiogenic cells (CACs) were isolated from blood samples donated by patients undergoing clinically indicated procedures [10]. Mononuclear cells were isolated using density-gradient centrifugation (Histopaque 1077; Sigma-Aldrich) and placed in culture for 4-6 days in endothelial basal media (EBM-2; Clonetics) supplemented with EGM-2-MV-SingleQuots (Clonetics). CACs were harvested by mechanical dissociation for experimentation within 7 days of starting culture. Commercially sourced human umbilical vein endothelial cells (HUVECs) were cultured according to the manufacturer's directions (Lonza).

Antigenic Profiling

Flow cytometry (Guava easyCyte 8HT flow cytometer; Millipore) was used to confirm EDC phenotype using monoclonal antibodies and similarly conjugated isotype-matched controls for abcg2 (FAB995P, R&D Systems), αSMA (ab66133, Abcam), Cadherin 11 (FAB17901G, R&D Systems), CD29 (FAB17781P, R&D Systems), CD31 (FAB3567F, R&D Systems), CD44 (FAB4948P, R&D Systems), CD51 (FAB3050A, R&D Systems), CD79 (FMC020, R&D Systems), CD73 (FMC020, R&D Systems), CD90 (FMC020, R&D Systems), CD105 (FMC020, R&D Systems), CD133 (130-090-826, Miltenyi Biotec), CD146 (FAB932F, R&D Systems), CD166 (FAB6561P, R&D Systems), c-Kit (9816-11, Southern Biotech), DDR2 (ab63337, Abcam), Nestin (IC1259F, R&D Systems), PDGFRα (FAB1264A, R&D Systems), SSEA-1 (FAB2155A, R&D Systems) and a cocktail of hematological markers that included CD11b, CD34, CD45 and CD79A (FMC020, R&D Systems). A minimum of 20,000 events were detected after fluorescent compensation using unlabeled controls. Positive cells were defined as the percentage of the population falling above the 99th percentile of the relevant isotype control (FlowJo v. 10, TreeStar Inc.).

Conditioned Media for Angiogenesis, CAC Migration, and Paracrine Profiling

Conditioned media was obtained from EDCs after 48 hours of culture in 1% oxygen 1% serum conditions. The paracrine signature of EDCs was initially profiled using an unbiased protein array (RayBio, USA). Follow-up confirmatory quantification was performed using a multiplex assay (BioPlex, USA) for the 6 most abundant cytokines produced by EDCs [7, 10]. The capacity of EDCs to promote angiogenesis was assessed using a growth factor depleted matrigel assay (ECM625, Millipore). HUVECs were seeded on matrigel with stem cell conditioned media or serum free DMEM supplemented with 100 mM VEGF (positive media control). After 18 h of incubation, each well was imaged and reconstructed using imaging software to allow for measures of cumulative tubular growth (NeuronJ; National Institutes of Health) [9, 10]. Stem cell recruitment was assessed by plating 4,000 human CACs suspended in serum-free DMEM into the upper well of a fibronectin coated trans-well plate (24 wells, 3.0 mm pores; Corning) with EDC conditioned media placed in the bottom well. Serum free DMEM containing 100 ng VEGF was used as an unbiased control to normalize individual variations in CAC migration. After 24 h of normoxic incubation, CACs that had successfully migrated through the polycarbonate membrane were fixed (4% para-formaldehyde) and nuclei were stained with 4',6-diamidino-2-phenylindole (DAPI; Sigma Aldrich). Fluorescent microscopy (10× magnification, 6 random fields) was used to determine the average number of cells per random field (Image J, ICTN plug-in, National Institutes of Health) [9, 10].

Cardiogenic Differentiation

The effect of variable culture conditions on the ability of EDCs to adopt a cardiac phenotype was assessed by plating 20,000 cells/cm$^2$ within cardiogenic media [7, 10, 11]. Cardiogenic media consisted of low glucose Dulbecco's Modified Eagle media, MCDB-201 media, dimethylsulfoxide, L-ascorbic acid, 0.01% ITS liquid media supplement, linoleic acid-albumin, penicillin-streptomycin, dexamethasone, 2-mercaptoethanol, recombinant human fibroblast growth factor 8b, recombinant human fibroblast growth factor 4, recombinant human protein Dickkopf-related protein 1 and recombinant human bone morphogenetic protein 2 [20]. After 7 days of culture, cells were harvested for flow cytometry (alpha smooth muscle actin (α-SMA; ab125266; Abcam), cardiac troponin T (cTnT, ab66133; Abcam) or von Willebrands Factor (vWF; 11778-1-AP; ProteinTech)).

In Vivo Testing

Experimental myocardial infarctions were performed in 39 male non-obese diabetic severe combined immunodeficient (NOD-SCID) mice by permanent ligation of the left coronary (LC) artery under a protocol approved by the University of Ottawa Heart Animal Care Service [7-10, 18, 21, 27]. Animals were injected with buprenorphine (0.05 mg/kg; subcutaneous) 1 hour prior to surgery and twice daily thereafter for 3 days. During the ligation, mice were intubated, anesthetized using isoflurane and maintained at physiologic temperatures. Upon closure, animals were injected with 0.5 cc of saline (subcutaneous). Seven days after ligation, 100,000 EDCs were injected into the myocardium along the infarct border and at the cardiac apex using transthoracic echocardiographic guidance (VisualSonics). Five mice died prior to completion of the study and were excluded from analysis (n=3 serum EDC-treated mice and n=2 SF EDC-treated mice). Left ventricular ejection fraction was evaluated 21 and 28 days after LC ligation to assess the functional effects of each cell therapy. After the last assessment of myocardial function, the mice were euthanized and hearts excised for histology or quantitative polymerase chain reaction (qPCR) analysis. Myocardial retention of transplanted cells was assessed in a subset of mice using qPCR for noncoding human alu repeats [9, 10]. Left ventricular genomic DNA was extracted, and qPCR was performed with transcript-specific hydrolysis primer probes. The remaining hearts were fixed with 4% paraformaldehyde, embedded in optimal cutting temperature compound (OCT) and sectioned. Tissue viability within the infarct zone was calculated from Masson's trichrome (Life Technologies) stained sections by tracing the infarct borders manually and using ImageJ software to calculate the percent of viable myocardium within the overall infarcted area [7-10, 18, 27]. EDC engraftment was confirmed by staining sections for human nuclear antigen (HNA; SAB4500768, Sigma-Aldrich) while EDC fate was established by staining sections for co-segregation with alpha smooth muscle actin (α-SMA; ab125266; Abcam), cardiac troponin T (cTnT, ab66133; Abeam) or von Willebrands Factor (vWF; 11778-1-AP; ProteinTech). Contributions of EDC therapy to capillary density were assessed by staining sections for isolectin B4 (B-1205, Vector Laboratories). All functional evaluations were conducted and analyzed by investigators blinded to the animal's treatment group.

EDC Stability and Delivery Testing

A French 11Fr (3.7 mm) TREK Coronary Dilation Catheter (Abbott Vascular) and a French 8Fr (2.7 mm) NOGA MyoStar intramyocardial Injection Catheter (Biosense Webster) was used to assess the impact of catheter delivery on cell viability. After coating the internal channel of both catheters with 25% human albumin (A2153, Sigma), harvested EDCs were suspended in Plasmalyte A (2B2544X, Baxter) with 2.5% human albumin for catheter delivery. Viability of the 2 million cells injected through the internal channels followed by viability testing (Trypan Blue) and delivery counts. The long-term stability of EDCs for transport between institutions was established using EDCs drawn up into BD Luer-Lok syringes and stored at 4 degrees Celsius for 18 hours. Cell viability using Trypan Blue (H7901, Sigma) exclusion was determined at time 0 (prior to loading the syringes) and after 18 hours.

Statistical Analysis

Data are expressed as mean±standard error of the mean. To determine if differences existed within groups, data was analyzed by a one-way ANOVA. If such differences existed, Bonferroni's corrected t-test was used to determine the group(s) with the difference(s) (Prism 6.01, GraphPad). Differences in categorical measures were analyzed using a Chi Square test. A final value of P≤0.05 was considered significant for all analyses.

Results

Figure 4:
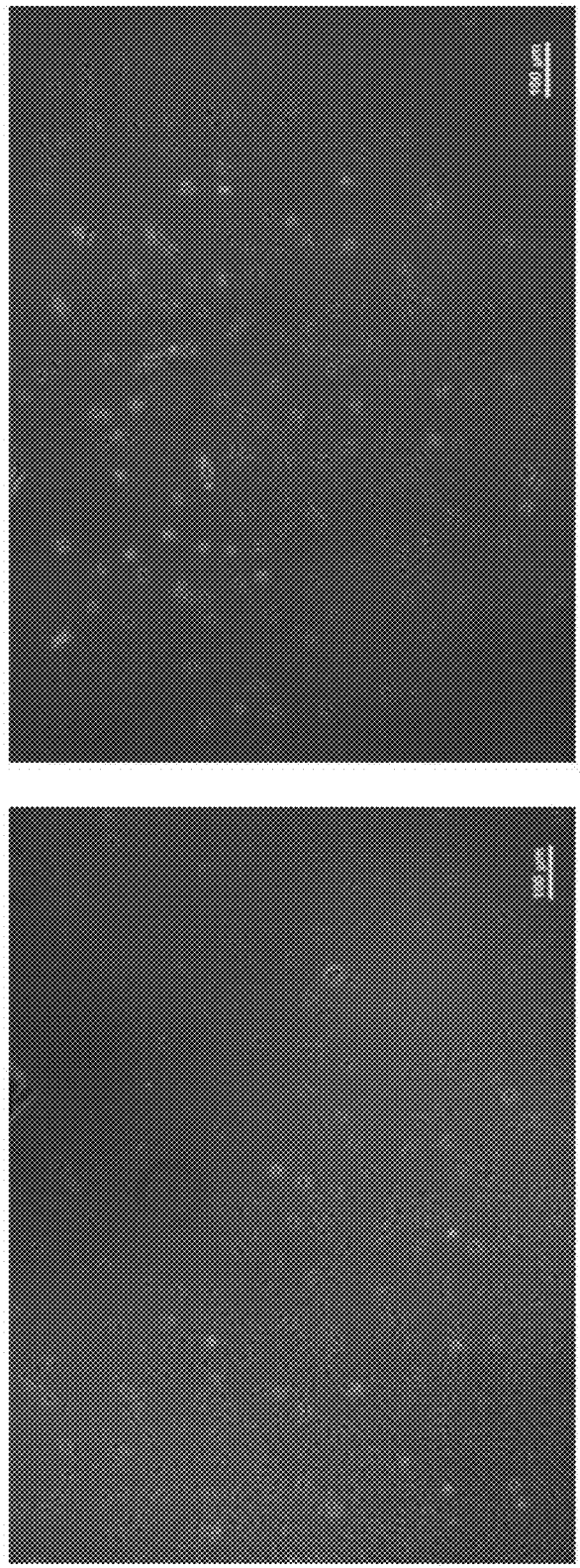
FIG. 4 shows representative brightfield images of serum and serum free cultured EDCs. Shown are typical brightfield images of the serum and serum free cultured EDCs taken 24 hours after harvest from the explant culture and re-plated on fibronectin coated cultureware. The first collection of cells from explant culture are shown in these images. These images suggest that EDCs cultured in serum free media are smaller and more homogeneous than those cultured in standard serum-dependent media.
Figure 4:
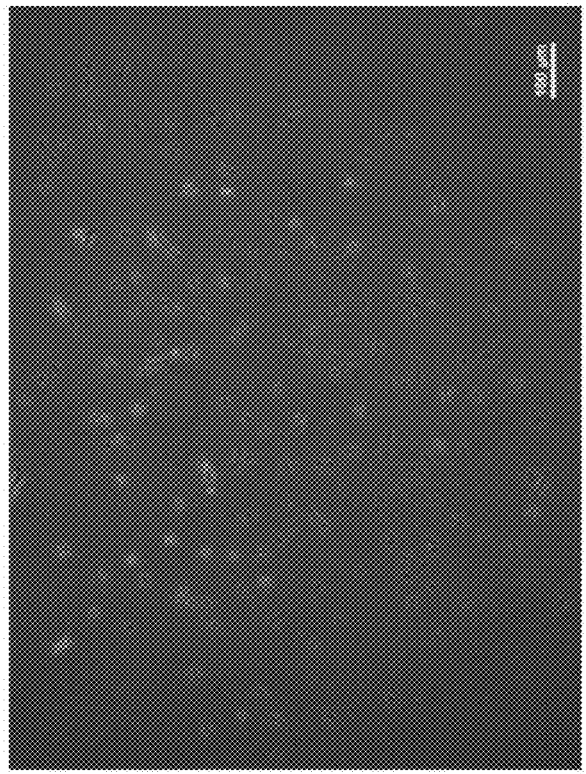

SF GMP Compatible Culture Conditions do not Alter EDC Culture Yields or Phenotype As shown in Table 5, atrial appendages or ventricular biopsies were harvested from patients undergoing clinically indicated cardiac surgery or post transplant surveillance, respectively. Primary EDC cultures were established by plating half of each atrial appendage specimen in standard serum-supplemented media or SF medium (50:50 split by mass). Brightfield images demonstrated EDCs that spontaneously emerged from tissue plated in SF media were smaller and more uniform in size (FIG. 4). This impression was confirmed through flow analysis of the forward (a correlate of cell surface area or size) and side (a correlate of granularity or internal complexity) scatter within harvested cells (FIG. 1A). EDCs cultured in SF medium demonstrated a lower forward scatter and reduced elliptical area of 95% containment (46±6 versus 103±7 square units for cells cultured in CEM, arbitrary units; p=0.002); suggesting that EDCs cultured in SF medium are smaller and more homogeneous than those cultured in standard serum-dependent media.

TABLE 5

Clinical characteristics of patients enrolled.

| Column 1 | Atrial Appendage donors (n = 11) | Ventricular Biopsy donors (n = 6) |
|---|---|---|
| Age (yrs) | 67 ± 3 | 52 ± 7 |
| BMI (kg/m2) | 29 ± 2 | 29 ± 1 |
| Gender (% male) | 63% | 67% |
| Diabetes | 63% | 17% |
| Hypertension | 82% | 17% |
| Dyslipidemia | 82% | 33% |
| Ongoing smoking | 0% | 0% |
| Thyroid disease | 10% | 33% |
| Peripheral vascular disease | 20% | 0% |
| Coronary artery disease | 82% | 17% |
| History of MI | 55% | 17% |
| Valvular heart disease | 36% | 50% |
| Congestive heart failure | 18% | 0% |
| NYHA class | 1.7 ± 0.4 | — |
| LV ejection fraction | 45 ± 6 | — |
| CCS class | 2.2 ± 0.6 | — |
| Creatine (umol/L) | 94 ± 18 | 92 ± 14 |
| Hemoglobin A1c | 6.6 ± 0.5 | 6.5 ± 0.5 |
| Medications: | | |
| Anti-platelet therapy | 100% | 100% |
| Beta-blocker | 73% | 50% |
| Statins | 91% | 83% |
| ACEI or ARB | 100% | 67% |

BMI = Body Mass Index;
MI = Myocardial infarction;
NYHA = New York Heart Association;
CCS = Canadian Cardiovascular Society;
ACEI = Angiotensin-converting-enzyme inhibitor;
ARB = Angiotensin II receptor blocker.

In contrast to previous work demonstrating divergent culture practices having profound effects on EDC biology [13-15], transitioning tissue explant culture from commercial grade collagenase IV to GMP compliant collagenase I/II did not significantly influence either overall cell culture yields (200±54 vs. 208±56×105 cells per mg tissue plated, respectively; p=0.92) or the major sub-population content at each serial harvest from the plated tissue (FIG. 1B). Culture of atrial appendage biopsies within SF conditions did not alter the overall cell culture yields as compared to standard serum culture (190±30 vs. 220±40×105 cells per mg tissue plated, respectively; p=0.57).

The effects of SF GMP conditions on the phenotypic signature of EDCs was investigated using a custom flow cytometry panel to evaluate expression of cardiac, endothelial, hematopoietic, mesenchymal and stem cell identity. As depicted in FIGS. 1C and 1D, SF conditions had only minor effects on the CD29, CD44, CD31 and Nestin content of EDCs.

Given that EDC culture is inherently limited by a constant culture output return proportional to the scale of production [11], the influence of straightforward EDC sub-culture within adherent cell cultures was investigated as a means of attaining clinically meaningful cell "doses" (exSF group). Plating of EDCs within SF media provided a 5.5±1.1-fold increase in cell numbers over 7 days with a population doubling time of 73±11 hours. With the exception of a minor decline in the proportion of SSEA-1+ cells (Δ1.0±0.1%, p=0.01 vs SF culture), static expansion within SF media had negligible effects on the antigenic profile of EDCs.

Tissue source did not alter the proliferative capacity of EDCs from plated tissue as culture yields from ventricular biopsies were maintained in the SF medium (1.7±0.3 vs. 1.2±0.5 million cells cultured per biopsy sample; p=0.45 vs. culture in media with serum).

Taken together, this data suggests that serum-free xenogen-free culture conditions supports ex vivo proliferation of EDCs from multiple tissue sources with negligible effects on the phenotypic signature of cells expanded to clinically relevant doses.

Figure 10:
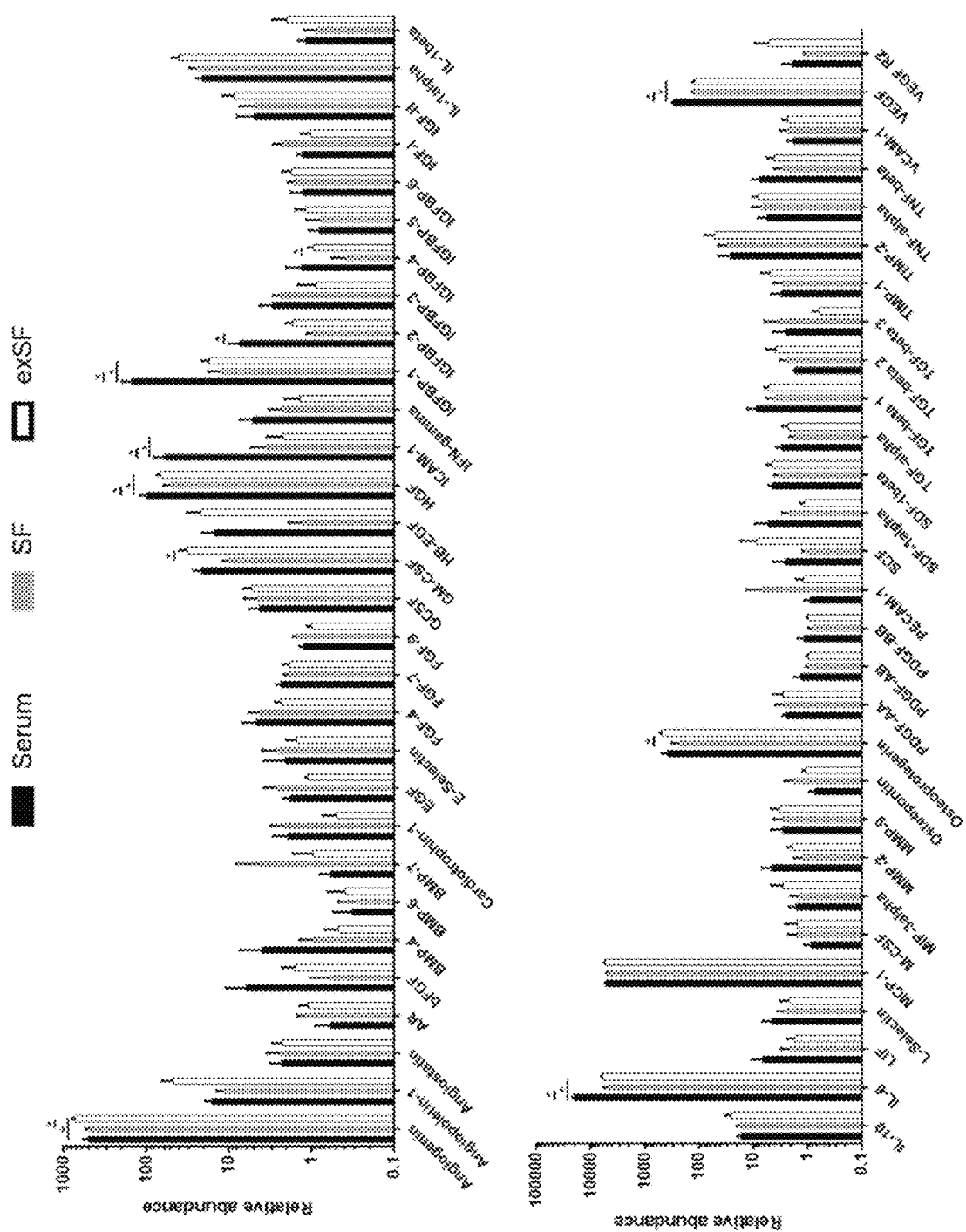
FIG. 10 shows results of proteomic profiling of cytokine content within conditioned EDC conditioned media (relative abundance between Serum, SF, and exSF shown; *p≤0.05). Results indicate that SF culture conditions tested had minor effects on cytokine production.

Effect of SF GMP Compatible Culture Conditions on the Regenerative Performance of EDCs The effects of GMP SF compatible conditions on the regenerative potency of the initial and expanded EDC cultures was investigated using established in vitro measures of indirect and direct cardiac repair [7, 9, 10, 22, 27]. As shown in FIG. 10, widespread unbiased profiling of the cytokine proteome within EDC conditioned media demonstrated that SF culture conditions had minor effects on cytokine production that generally favored cells cultured in serum conditions. Quantitative analysis using multiplex profiling confirmed this impression (FIG. 2A) as the initial or serum free EDC conditioned media demonstrated equivalent secretion of stromal cell derived factor 1α (SDF-1α) and stem cell factor (SCF) with reduced production of hepatic growth factor (HGF; 82±2% less; p=0.003), interleukin 6 (IL-6; 96±2% less; p=0.001) and vascular endothelial growth factor A (VEGF-A; 50±5% less; p=0.02) by SF cells. Similar to effects seen on the phenotypic profile of EDCs following expansion to clinically relevant cell "doses", expansion within serum free media had limited appreciable effects on the paracrine signature of EDCs.

Given recent evidence suggesting that a portion of cardiac-derived cell regenerative potency is dependent upon the secretion of transplanted cell derived exosomes [29-31], the micro-particle content within EDC conditioned media was profiled. Nanocyte tracking analysis revealed that SF culture conditions had no effect on particle content (840±173 vs 575±110 million particles/ml, p=0.25) or size (156±7 vs. 148±6 nm, p=0.41 vs. serum conditions) within EDC conditioned media. Similarly, expansion of SF cultured cells had no effect on micro-particle content (800±80 million particles/ml, p=0.53 vs. SF EDCs) or size (1.43±4, p=0.5).

Figure 2:
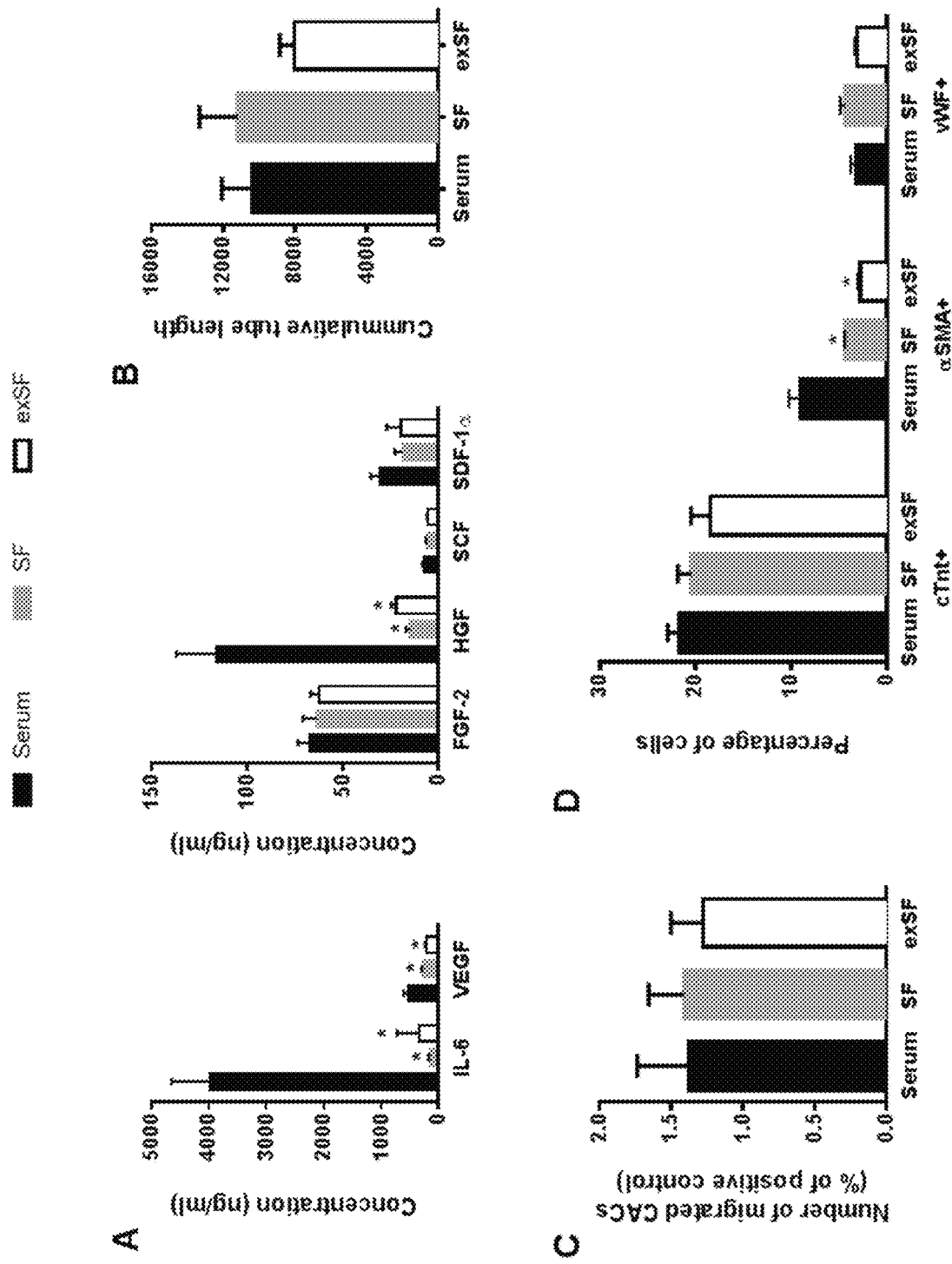
FIG. 2 shows influence of serum free culture conditions on the paracrine signature and differentiation of EDCs. (A) Multiplex cytokine profiling of conditioned media from standard 20% serum, serum free media and expanded serum free EDCs (mean±SEM, *p<0.05 vs. standard 20% serum culture; n=4 explant cultures). (B) Conditioned media from serum free and expanded serum free EDCs had negligible effects on the cumulative tubule length of HUVECs after 18 hours in culture (mean±SEM, n=5 explant cultures performed in triplicate with 6 random fields per sample assayed). (C) Conditioned media from serum free and expanded serum free EDCs had negligible effects on the number CACs attracted through a transwell assay (mean±SEM, n=5 explant cultures performed in triplicate with 6 random fields per sample assayed and using a single donor sourced CAC line). (D) EDCs cultured and expanded in serum free conditions demonstrated a reduced ability to adopt a smooth muscle fate (alpha smooth muscle actin, αSMA) relative to standard 20% serum cultured EDCs. In contrast, serum free culture and expansion of EDCs had negligible effects on the ability of cells to adopt a myogenic (cardiac troponin T, cTNT) or endothelial (von Willebrand Factor, vWF) identity. Data is shown as mean±SEM with 5 explant cultures (*p<0.05 vs. standard 20% serum culture)

Despite the noted effects by SF conditions on the cytokine profile of EDCs, application of conditioned media to a HUVEC cytokine depleted matrigel angiogenesis assay or CAC transwell cultures demonstrated that altered EDC culture conditions had negligible effects on angiogenesis (FIG. 2B) or CAC recruitment (FIG. 2C).

The influence of serum free culture on the ability of EDCs to adopt a cardiac phenotype was investigated after 7 days of culture in conditions known to favor a cardiac identity [7, 8, 11, 20]. Flow cytometry revealed an equivalent propensity for SF cells to adopt a cardiomyocyte lineage (cTnT+; 20±1% of cells, p=0.55 vs. standard EDCs) and endothelial lineage (vWF+; 4.3±0.5% of cells, p=0.22 vs. standard EDCs) but a reduced tendency toward smooth muscle differentiation (αSMA+, 4.3±0.1% of cells, p=0.017 vs. standard EDCs, FIG. 2D). Expansion of SF cultured cells did not influence the expression of cTNT, vWF or αSMA after culture in cardiogenic conditions (p=ns vs. EDCs from SF conditions).

SF GMP Compatible Culture Conditions Enhance EDC-Mediated Cardiac Repair

Figure 6:
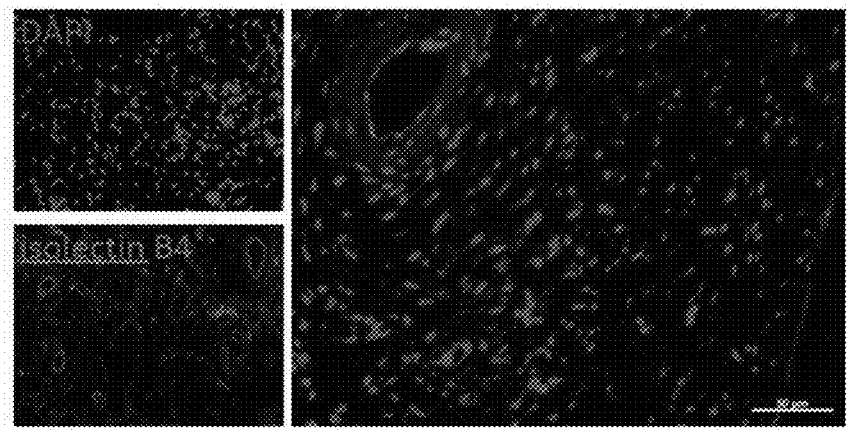
FIG. 6 shows representative peri-infarct images demonstrating capillary density in sections obtained from animals randomized to transplant of serum, serum-free or expanded serum free cultured EDCs. Immunohistochemical single and merged images of peri-infarct sections demonstrating nuclei (DAPI) and myocardial vessels (isolectin B4). Scale=50 um.
Figure 6:
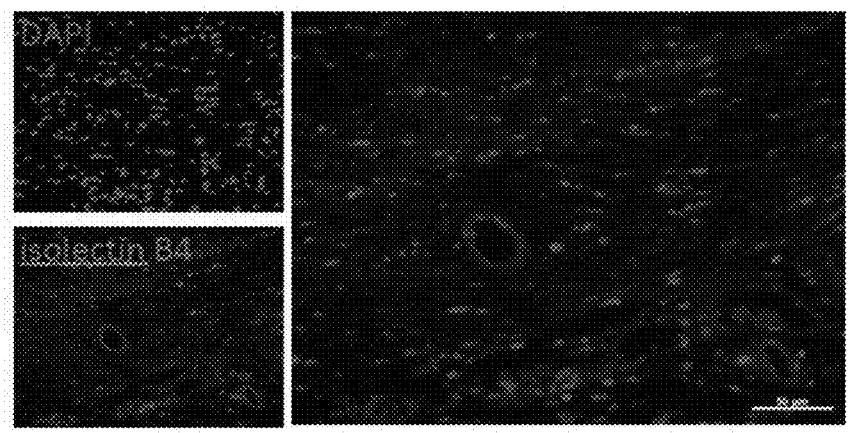
Figure 6:
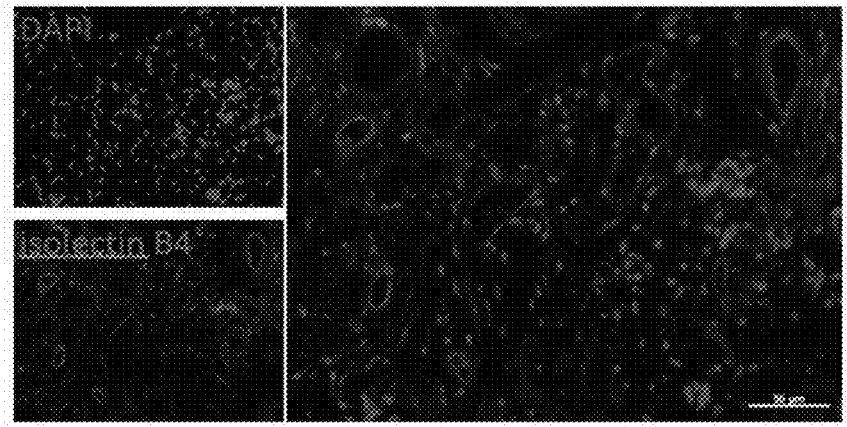
Figure 7:
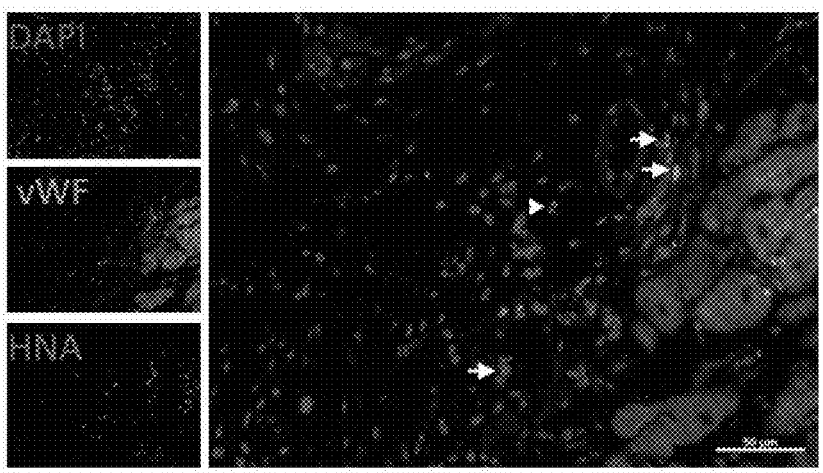
FIG. 7 shows representative peri-infarct images demonstrating cells of human origin expressing markers of endothelial fate in sections obtained from animals randomized to transplant of serum, serum-free or expanded serum free cultured EDCs. Immunohistochemical single and merged images of peri-infarct sections demonstrating nuclei (DAPI), transplanted cell origin (human nuclear antigen; HNA) and endothelial fate (von Willebrands factor; vWF). Arrows indicate single cell co-segregation of HNA and vWF markers. Scale=50 um.
Figure 7:
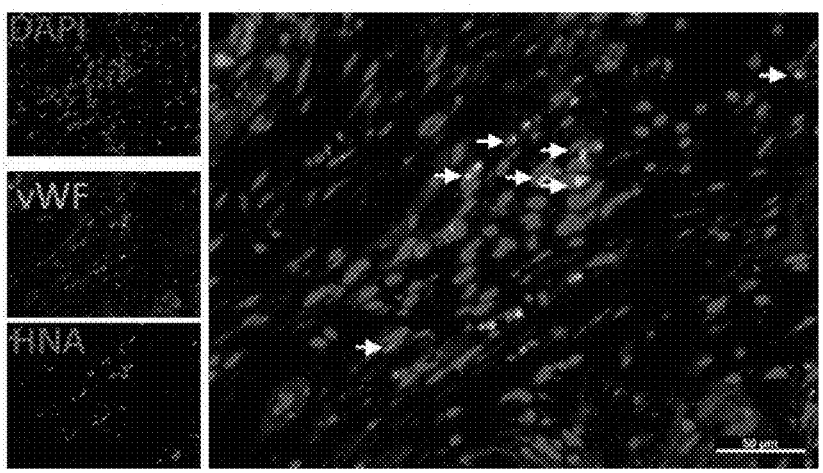
Figure 7:
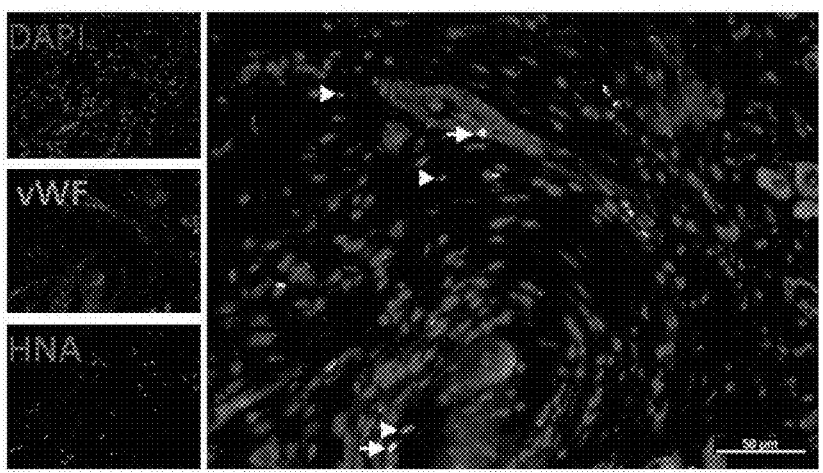
Figure 8:
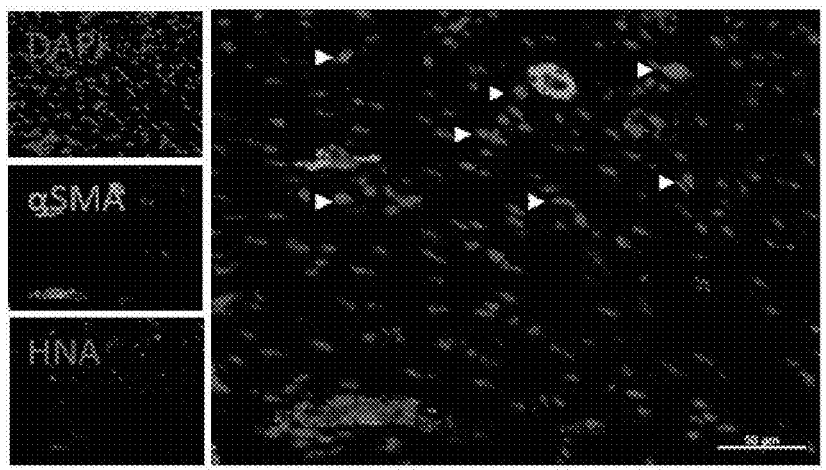
FIG. 8 shows representative peri-infarct images demonstrating cells of human origin expressing markers of smooth muscle fate in sections obtained from animals randomized to transplant of serum, serum-free or expanded serum free cultured EDCs. Immunohistochemical single and merged images of peri-infarct sections demonstrating nuclei (DAPI), transplanted cell origin (human nuclear antigen; HNA) and smooth muscle fate (alpha smooth muscle actin; αSMA). Arrows indicate single cell co-segregation of HNA and αSMA markers. Scale=50 um.
Figure 8:
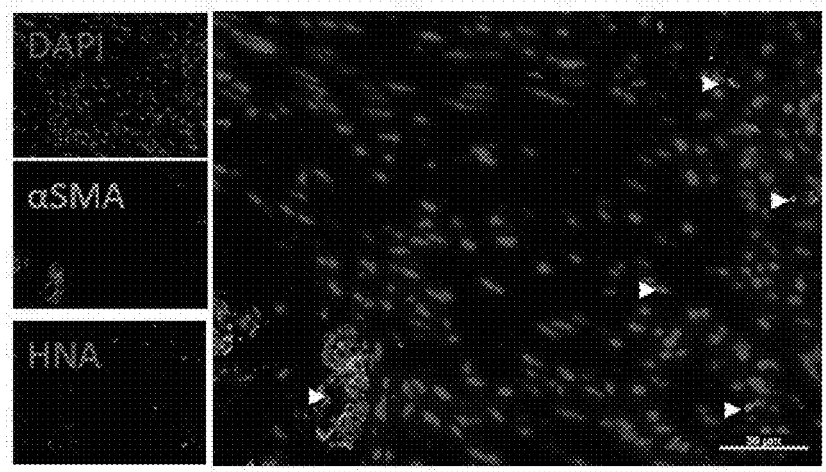
Figure 8:
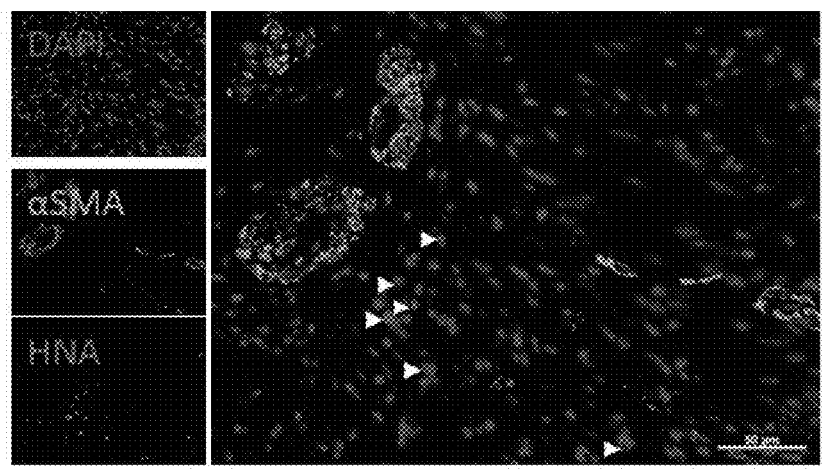
Figure 9:
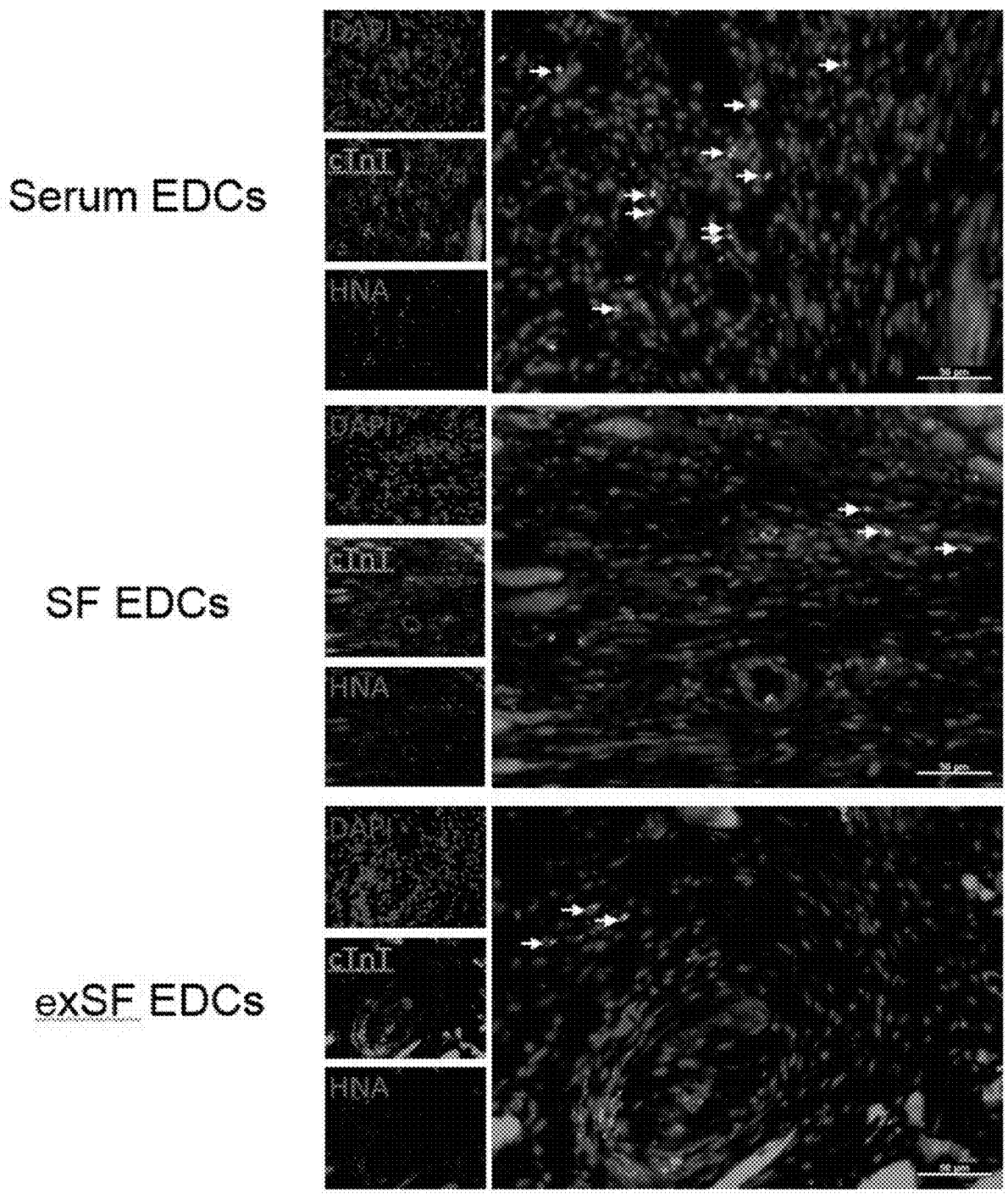
FIG. 9 shows representative peri-infarct images demonstrating cells of human origin expressing markers of cardiomyocyte fate in sections obtained from animals randomized to transplant of serum, serum-free or expanded serum free cultured EDCs. Immunohistochemical single and merged images of peri-infarct sections demonstrating nuclei (DAPI), transplanted cell origin (human nuclear antigen; HNA) and cardiomyocyte fate (cardiac troponin T; cTNT). Arrows indicate single cell co-segregation of HNA and cTNT markers. Scale=50 um.

The influence of SF culture and EDC expansion on therapeutic cardiac repair was investigated in a series of immunodeficient mice randomized to echocardiographic guided injection of serum, SF or expanded SF EDCs 1 week after LC ligation. As shown in Table 6, all animals had equivalent ejection fractions, chamber dimensions and stroke volumes 7 days post LC ligation. Animals treated with SF EDCs showed superior improvements in echocardiographic ejection fraction 3 weeks after cell treatment compared to animals receiving traditional serum cultured EDCs (48±3 vs. 40±2%, respectively; p=0.046, FIG. 3A and Table 6). The regenerative advantages conferred by administering cells cultured in SF conditions was reduced in animals that received equivalent "cell doses" of expanded SF EDCs (41±2%; p≤0.05 vs. SF EDCs) to an extent that was comparable to animals who received cells cultured in standard serum conditions. Despite these clear improvements in myocardial function, administration of SF EDCs had no effect on the final scar burden (FIG. 3B and FIG. 5) or capillary densities (FIG. 3C and FIG. 6).

Figure 3:
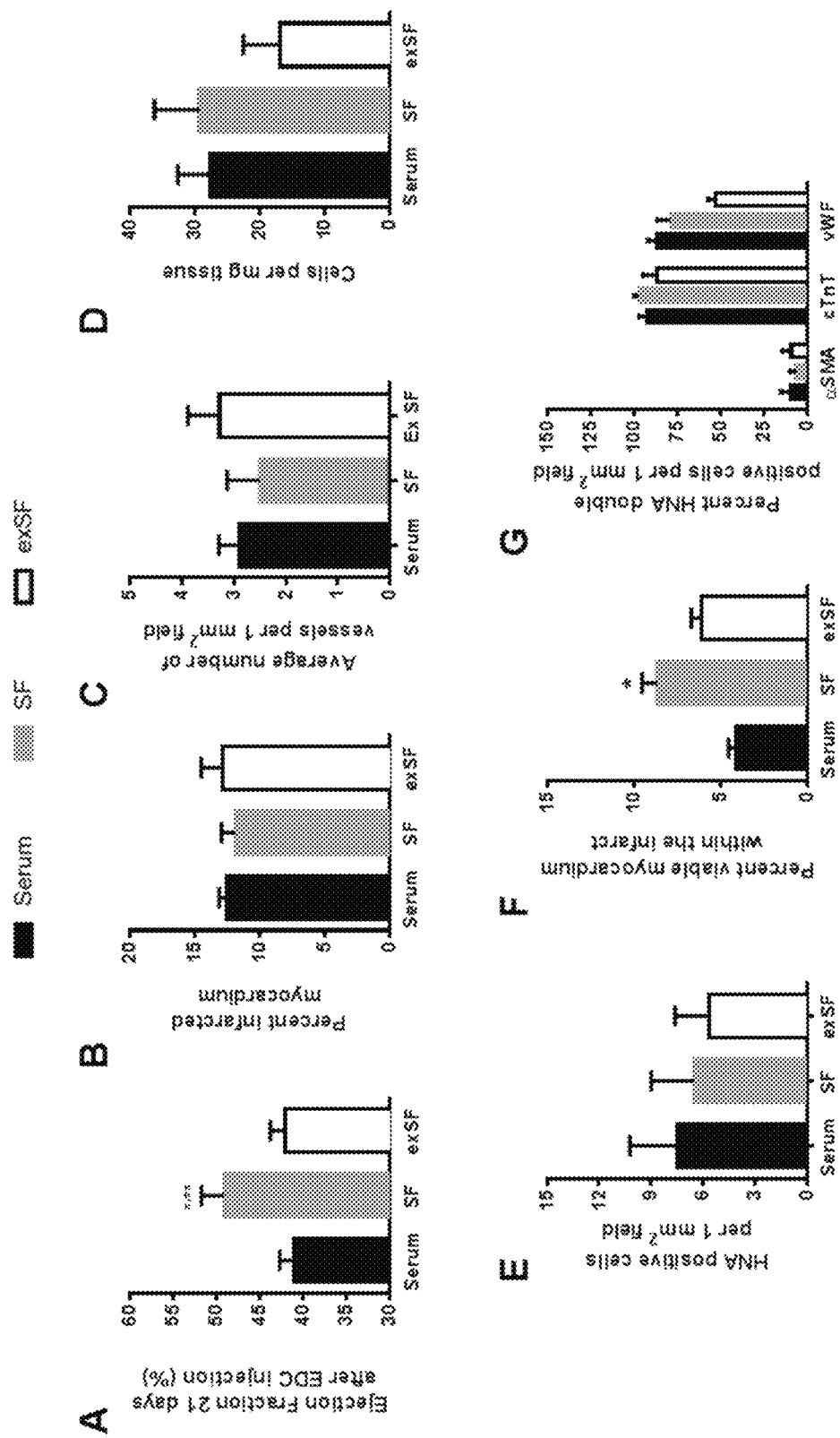
FIG. 3 shows transplant of EDCs from serum free culture conditions. (A) Transplant of 100,000 serum free EDCs into immunodeficient mice 1 week after left coronary ligation provided marked increases in myocardial function 21 days after cell injection as compared to equivalent numbers of EDCs cultured in 20% serum or expanded serum free EDCs (mean±SEM, *p<0.05 vs. 20% serum cultured EDCs, **p<0.05 vs. expanded serum free cultured EDCs; n=10-13 mice per group). (B) Effects of serum free EDC transplantation on the overall percentage infarcted myocardium as determined from Masson's trichrome staining (mean±SEM, n=5 mice per group with 3 adjacent sections averaged per mouse). (C) Effects of serum free EDC transplantation on angiogenesis (mean±SEM, n=5 mice per group with 3 adjacent sections averaged per mouse). Effects of serum free EDC transplantation on engraftment as determined using qPCR for retained human alu sequences (D; mean±SEM, n=6 mice per group) or random field counts of human nuclear antigen (HNA) positive cells (E; mean±SEM, n=8 mice per group with 3 random fields sampled within 3 adjacent sections per mouse). (F) Effects of serum free EDC transplantation on the percentage of viable myocardium within the infarct zone (mean±SEM, *p≤0.05 vs. 20% serum cultured EDCs; n=6 mice per group with 3 adjacent sections averaged per mouse). (G) Effects of serum free EDC transplantation on the fate of engrafted EDCs within the peri-infarct zone (mean±SEM, n=3 mice per group with 3 adjacent sections averaged per mouse)

Furthermore, treatment with SF cultured EDCs provided no detectable influence on the modest long-term engraftment of transplanted cells (FIGS. 3D and 3E). The functional echocardiographic benefits seen after administration of SF cultured EDCs were attributable to increases in viable myocardium within the infarct itself—hinting that SF cultured EDCs promoted larger degrees of newly formed myocardium within the treatment zone (FIG. 3F). To provide insight into the final fate of transplanted cells, immunohistochemistry was performed to identify cells positive for human nuclear antigen (HNA) in conjunction with markers indicative of cardiomyocyte (cTnT), smooth muscle (αSMA) or endothelial vascular (vWF) lineages. As depicted in FIG. 3G and FIGS. 7-9, localized clusters human cells positive for cTnT and vWF were seen in all groups while relatively fewer human cells of smooth muscle identity were observed. Taken as a whole, these results suggest that administration of SF cultured cells may provide an enhanced cell product that boosts recovery within the infarcted tissue without influencing the final scar burden, vascularity or fate of transplanted cells. Furthermore, expansion within SF media provides greater amounts of cells to be delivered but attenuates that ability of cells to promote post-infarct cardiac function.

TABLE 6

Echocardiographic measurements of left ventricular function 7 and 28 days after left coronary ligation.

|  | Left ventricular end diastolic volume (ml) | Left ventricular end systolic volume (ml) | Stroke Volume (ml) | Ejection Fraction (%) | Fractional Area Shortening (%) |
| --- | --- | --- | --- | --- | --- |
| 7 days post LAD ligation | | | | | |
| Serum (n = 13) | 52.6 ± 3.9 | 34.8 ± 3 | 17.8 ± 1.7 | 33.7 ± 2.3 | 19.4 ± 1.8 |
| SF (n = 10) | 51.6 ± 2.7 | 33.6 ± 2.2 | 18 ± 1.2 | 35.1 ± 1.7 | 21.6 ± 1.4 |
| exSF (n = 12) | 56.1 ± 4.4 | 37 ± 3.4 | 19.1 ± 1.8 | 34.4 ± 2.2 | 20.9 ± 1.7 |

TABLE 6-continued

Echocardiographic measurements of left ventricular function
7 and 28 days after left coronary ligation.

|  | Left ventricular end diastolic volume (ml) | Left ventricular end systolic volume (ml) | Stroke Volume (ml) | Ejection Fraction (%) | Fractional Area Shortening (%) |
|---|---|---|---|---|---|
| 28 days post LAD ligation | | | | | |
| Serum (n = 13) | 54.1 ± 2.5 | 32.6 ± 2.5 | 21.4 ± 0.6 | 40.8 ± 2.3 | 25 ± 1.5 |
| SF (n = 10) | 49.9 ± 3.1 | 26.5 ± 2.7 | 23.4 ± 1.1 | 47.9 ± 2.7*,** | 30.2 ± 1.9* |
| exSF (n = 12) | 58.9 ± 4.4 | 35.1 ± 3.8 | 23.8 ± 1 | 41.4 ± 2.4 | 26 ± 1.7 |

*p < 0.05 vs serm
**p < 0.05 vs exSF
*p ≤ 0.05 vs. serum cultured EDCs,
**p ≤ 0.05 vs. expanded serum free cultured EDCs.

Clinical Delivery and Brief Suspension Storage of EDCs Does Not Influence Cell Viability To enable the straightforward clinical implementation of cultured EDCs, the impact of catheter delivery via clinical intra-coronary and transendocardial routes was evaluated. Counts of viable cells before and after intra-coronary catheter delivery demonstrated successful delivery of 96±2% of EDCs with 95±2% of cells remaining viable after delivery. Similarly, delivery of cells through a NOGA transendocardial catheter demonstrated successful delivery of 94±1% of cells with 97±1% of cells remaining viable after delivery. Tests of EDC stability revealed negligible changes in viable cell counts after 18 hours in suspension at 4 degrees Celsius (96±2% p=0.07 vs. baseline viability) with no attrition attributable to serum free culture conditions (p=0.58 vs. serum cultured EDCs).

Although cardiac stem cell therapy has progressed rapidly from bench to bedside over the past decade [5, 6, 23], straightforward clinical translation has been hampered by reliance on traditional culture conditions which often include ill-defined or xenobiotic components. Overcoming these barriers may represent a critical step in the translation of cardiac-based cell therapies into clinical use. As described herein, cultures of the first outgrowth of plated cardiac tissue (EDCs) were undertaken to investigate the effects of a serum-free, xeno-free culture system on proliferation and product identity. EDCs were chosen as the cell type to study as they represent the initial cell product used prior to antigenic selection [24] and/or prolonged inductive culture [25]. Previous work has shown that EDCs provide complimentary collection of cell types that provide degrees of myocardial repair equivalent to CDCs while retaining a. 1000-fold greater capacity to adopt a cardiac fate [11], making EDCs a valuable tool to detect the early effects of divergent cell culture practices [15].

The cell culture outcomes outlined above suggest that serum free conditions yield a cell product morphologically similar to standard cardiac explant conditions. Interestingly, the smaller and more homogeneous cell product derived using SF xenogen-free conditions likely results from stable consistent recombinant cytokines found in the defined media while retaining antigenic identities at levels consistent with traditional cultures. Notably, the use of recombinant serum free media also avoids exposing human cells to bovine-sourced exosomes—a component of traditional media that remains poorly defined.

These data and pre-clinical work on allogeneic bone marrow derived mesenchymal stromal cell culture (Cellular Immunotherapy for Septic Shock: A Phase I Trial (CISS), NCT02421484) suggest that Nutristem XF may provide consistent culture outcomes. Previous work by our group has identified that EDCs express important receptors (such as insulin-like growth factor 1 and SDF-1α) that may influence proliferation [7, 8]. It follows that, in certain embodiments, supplementation of commercial SF media formulations may be used to formulate media further tailored to EDC culture outcomes.

Interestingly, eliminating ill-defined bovine sourced cytokines or exosomes had marked effects on the cytokine profile of EDCs; suggesting that serum free recombinant cytokine conditions may permit cells to retain a more "human" or "natural" identity. Without wishing to be bound by theory, this effect very likely altered the manner in which EDCs mediated post infarct healing as reduced production of key cytokines (such as IL-6 or VEGF) and influence that manner in which transplanted cells interact with the damaged host. As shown above, delivery of a more homogenous cell-product may provide greater healing within scarred tissue, and/or better functional gains, under the conditions tested.

All references cited herein are herein incorporated by reference in their entirety.

One or more illustrative embodiments have been described by way of example. It will be understood to persons skilled in the art that a number of variations and modifications may be made without departing from the scope of the invention as defined in the claims.

REFERENCES

1. Alter D A, Ko D T, Tu J V et al. The average lifespan of patients discharged from hospital with heart failure. J Gen Intern Med. 2012; 27:1171-1179.
2. Lee D S, Schull M J, Alter D A et al. Early deaths in patients with heart failure discharged from the emergency department: a population-based analysis. Circ Heart Fail. 2010; 3:228-235.
3. Chugh A R, Beache G M, Loughran J H et al. Administration of cardiac stem cells in patients with ischemic cardiomyopathy: the SCIPIO trial: surgical aspects and interim analysis of myocardial function and viability by magnetic resonance. Circulation. 2012; 126:S54-S64.
4. Bolli R, Chugh A R, D'Amario D et al. Cardiac stem cells in patients with ischaemic cardiomyopathy (SCIPIO): initial results of a randomised phase 1 trial. Lancet. 2011; 378:1847-1857.
5. Malliaras K, Smith R R, Kanazawa H et al. Validation of contrast-enhanced magnetic resonance imaging to monitor regenerative efficacy after cell therapy in a porcine model of convalescent myocardial infarction. Circulation. 2013; 128:2764-2775.

6. Makkar R R, Smith R R, Cheng K et al. Intracoronary cardiosphere-derived cells for heart regeneration after myocardial infarction (CADUCEUS): a prospective, randomised phase 1 trial. Lancet. 2012; 379:895-904.
7. Tilokee E L, Latham N, Jackson R et al. Paracrine Engineering of Human Explant-Derived Cardiac Stem Cells to Over-Express Stromal-Cell Derived Factor 1alpha Enhances Myocardial Repair. Stem Cells. 2016.
8. Jackson R, Tilokee E L, Latham N et al. Paracrine Engineering of Human Cardiac Stem Cells With Insulin-Like Growth Factor 1 Enhances Myocardial Repair. J Am Heart Assoc. 2015; 4.
9. Molgat A S, Tilokee E L, Rafatian G et al. Hyperglycemia inhibits cardiac stem cell-mediated cardiac repair and angiogenic capacity. Circulation. 2014; 130:S70-S76.
10. Latham N, Ye B, Jackson R et al. Human Blood and Cardiac Stem Cells Synergize to Enhance Cardiac Repair When Cotransplanted Into Ischemic Myocardium Circulation. 2013:128:S1-S8.
11. Davis D R, Kizana E, Terrovitis J et al. Isolation and expansion of functionally-competent cardiac progenitor cells directly from heart biopsies. JMCC. 2010; 49:312-321.
12. Chimenti I, Gaetani R, Forte E et al. Serum and supplement optimization for EU GMP-compliance in cardiospheres cell culture. J Cell Mol Med. 2014; 18:624-634.
13. Shenje L T, Field L J, Pritchard C A et al. Lineage tracing of cardiac explant derived cells. PLoS ONE. 2008; 3:e1929.
14. Andersen D C, Andersen P, Schneider M et al. Murine "Cardiospheres" Are Not a Source of Stem Cells with Cardiomyogenic Potential. Stem Cells. 2009; 27:1571-1581.
15. Davis D R, Zhang Y, Smith R R et al. Validation of the cardiosphere method to culture cardiac progenitor cells from myocardial tissue. PLoS ONE. 2009; 4:e7195.
16. Rubio D, Garcia-Castro J, Martin M C et al. Spontaneous human adult stem cell transformation. Cancer Res. 2005; 65:3035-3039.
17. Shapiro A M, Ricordi C, Hering B J et al. International trial of the Edmonton protocol for islet transplantation. N Engl J Med. 2006; 355:1318-1330.
18. Mayfield A E, Tilokee E L, Latham N et al. The effect of encapsulation of cardiac stem cells within matrix-enriched hydrogel capsules on cell survival, post-ischemic cell retention and cardiac function. Biomaterials. 2014; 35:133-142.
19. Li T S, Cheng K, Malliaras et al. Expansion of human cardiac stem cells in physiological oxygen improves cell production efficiency and potency for myocardial repair. Cardiovasc Res. 2011; 89:157-165.
20. Ott H C, Matthiesen T S, Brechtken J et al. The adult human heart as a source for stem cells: repair strategies with embryonic-like progenitor cells. Nat Clin Pract Cardiovasc Med. 2007; 4 Suppl 1:S27-S39.
21. Latham N, Davis D R. Recent advances in cardiac stem cell therapy to restore ventricular function. In: Li R K, Weisel R D, eds. Cardiac regeneration and repair. United Kingdom: Woodhead Publishing Limited; 2014:163-195.
22. Davis D R, Smith R R, Marban E. Human Cardiospheres are a Source of Stem Cells with Cardiomyogenic Potential. Stem Cells. 2010; 28:903-904.
23. Malliaras K, Makkar R R, Smith R R et al. Intracoronary cardiosphere-derived cells after myocardial infarction: evidence of therapeutic regeneration in the final 1-year results of the CADUCEUS trial (CArdiosphere-Derived aUtologous stem CElls to reverse ventricUlar dySfunction). J Am Coll Cardiol. 2014; 63:110-122.
24. Bearzi C, Rota M, Flosoda T et al. Human cardiac stem cells. Proc Natl Acad Sci USA. 2007; 104:14068-14073.
25. Smith R R, Barile L, Cho et al. Regenerative Potential of Cardiosphere-Derived Cells Expanded From Percutaneous Endomyocardial Biopsy Specimens. Circulation. 2007; 115:896-908.
26. Cheng, K., D. Shen, B. Sun, K. Malliaras, R. Smith, S. Chowdhury, D. Duong, R. Makkarand E. Marban (2012). "Irrelevance of c-Kit-Positive Subpopulation to the Therapeutic Benefit of Human Cardiosphere-Derived Cells." Circulation126: A13259.
27. Mayfield A E, Fitzpatrick M E, Latham N et al. The impact of patient co-morbidities on the regenerative capacity of cardiac explant-derived stem cells. Stem Cell Res Ther. 2016; 7:60.
28. Mayfield A E, Tilokee E L, Latham N et al. The effect of encapsulation of cardiac stem cells within matrix-enriched hydrogel capsules on cell survival, post-ischemic cell retention and cardiac function. Biomaterials. 2014; 35:133-142.
29. Cambier L, de Couto G, Ibrahim A et al. Y RNA fragment in extracellular vesicles confers cardioprotection via modulation of IL-10 expression and secretion. EMBO Mol Med. 2017; 9:337-352.
30. de Couto G, Gallet R, Cambier L et al. Exosomal microRNA Transfer into Macrophages Mediates Cellular Postconditioning. Circulation. 2017.
31. Ibrahim A G, Cheng K, Marban E. Exosomes as critical agents of cardiac regeneration triggered by cell therapy. Stem Cell Reports. 2014; 2:606-619.

All references cited above and anywhere else herein are hereby incorporated by reference in their entirety.

What is claimed is:

1. A method for transitioning cardiac explant-derived stem cells (EDC) to serum-free (SF) and xenogen-free culture conditions, said method comprising: providing an initial cardiac explant, which has optionally been obtained from atrial appendages or myocardial, atrial, or ventricular biopsy, and which has been minced and digested with collagenase; plating the initial cardiac explant on a cell culture plate; culturing the plated cardiac explant in serum-free and xenogen-free medium; harvesting EDC cells surrounding or emerging from the plated cardiac explant using trypsin; and, without sphering of cells, performing static expansion of harvested EDC cells on fibronectin-coated cultureware in serum-free and xenogen-free medium; thereby transitioning cardiac EDC cells to serum-free (SF) and xenogen-free culture conditions.

2. The method of claim 1, wherein the collagenase is collagenase I/II.

3. The method of claim 1, wherein the cell culture plate is a fibronectin-coated plate.

4. The method of claim 1, wherein the culturing is performed at physiological oxygen tension of about 5%, or at ambient oxygen tension of about 21%.

5. The method of claim 1, wherein the culturing includes supplementing with serum for an initial period, followed by full replacement with serum-free and xenogen-free medium.

6. The method of claim 5, wherein the supplementing comprises supplementing with about 2% serum.

7. The method of claim 5, wherein the initial period is about 48 hours, or more.

8. The method of claim 1, wherein the cardiac explant-derived stem cells (EDC) are human.

9. The method of claim 1, wherein the collagenase, the cell culture plate, the serum-free and xenogen-free medium, the trypsin, the cultureware, or any combination thereof, are Good Manufacturing Practice (GMP)-grade.

10. The method of claim 1, wherein the serum-free and xenogen-free media is Nutristem XF.

11. The method of claim 1, wherein the trypsin is TrypLE Select.

12. The method of claim 1, wherein the static expansion is performed for about 7 days.

13. The method of claim 1, wherein the method comprises: performing a plurality of the harvesting step and static expansion step, followed by cryogenic storage of the thus obtained EDC cells; and recovering and pooling the cryogenically stored EDC cells.

14. The method of claim 13, wherein the harvesting and static expansion steps are performed up to 5 times.

15. The method of claim 13, wherein the pooled EDC cells are for administration to a subject in need thereof as a single intra-myocardial or intra-coronary injection, or as multiple intra-myocardial or intra-coronary injections.

16. The method of claim 15, wherein the pooled EDC cells are autologous for the subject.

17. The method of claim 1 which further comprises recovering a serum-free, xenogen-free cardiac explant-derived cell (EDC).

18. The method of claim 17, wherein the serum-free, xenogen-free cardiac explant-derived cell (EDC) is derived from an expanded EDC culture.

19. The method of claim 17 which further comprises providing the recovered serum-free, xenogen-free human cardiac explant-derived cell (EDC) produced in a kit that additionally comprises at least one of a serum-free and xenogen-free medium, a tool for injection of the EDC cells into the heart of a subject in need thereof, a collagenase, a cell culture plate, a trypsin, a cultureware, a vessel for the EDC cells, a differentiating signal or factor for causing the EDC cells to differentiate into cardiac tissue, instructions for culturing the EDC cells under serum-free and xenogen-free conditions, instructions for injecting the EDC cells into the heart of a subject in need thereof, or any combination thereof.

20. A method for treating heart failure and/or for repairing and/or regenerating cardiac tissue in a subject in need thereof, said method comprising: transplanting serum-free, xenogen-free human cardiac explant-derived cells (EDC) obtained by claim 17 into the subject; and allowing the EDC to repair or replace injured or lost tissue in the subject.

21. The method of claim 20, wherein the serum-free, xenogen-free cardiac EDC cells are administered by intra-myocardial or intra-coronary injection, the tissue is myocardium tissue, or both.

* * * * *